(12) United States Patent
Seifert

(10) Patent No.: US 12,281,312 B2
(45) Date of Patent: Apr. 22, 2025

(54) ANTI-FIBRINOGEN APTAMERS

(71) Applicant: Laboratoire Francais du Fractionnement et des Biotechnologies, Les Ulis (FR)

(72) Inventor: Alexander Seifert, Paris (FR)

(73) Assignee: Laboratoire Francais du Fractionnement et des Biotechnologies, Les Ulis (FR)

(*) Notice: Subject to any disclaimer, the term of this patent is extended or adjusted under 35 U.S.C. 154(b) by 410 days.

(21) Appl. No.: 17/389,878

(22) Filed: Jul. 30, 2021

(65) Prior Publication Data
US 2022/0098590 A1    Mar. 31, 2022

Related U.S. Application Data

(63) Continuation of application No. 16/320,770, filed as application No. PCT/EP2017/066940 on Jul. 6, 2017, now abandoned.

(30) Foreign Application Priority Data

Jul. 28, 2016 (EP) .................................. 16305983
Jul. 28, 2016 (EP) .................................. 16305984
Jul. 28, 2016 (EP) .................................. 16305985

(51) Int. Cl.
C12N 15/11      (2006.01)
C12N 15/10      (2006.01)
C12N 15/115     (2010.01)

(52) U.S. Cl.
CPC ........ *C12N 15/115* (2013.01); *C12N 15/1048* (2013.01); *C12N 2310/16* (2013.01); *C12N 2320/13* (2013.01); *C12N 2330/30* (2013.01)

(58) Field of Classification Search
CPC .............. C12N 15/115; C12N 2310/16; C12N 15/1048
See application file for complete search history.

(56) References Cited

U.S. PATENT DOCUMENTS

| | | | | |
|---|---|---|---|---|
| 2011/0111406 | A1* | 5/2011 | Igawa | A61P 37/00 435/69.6 |
| 2013/0022967 | A1* | 1/2013 | Takenaka | G01N 33/5308 536/23.1 |
| 2013/0184160 | A1 | 7/2013 | Wang et al. | |
| 2013/0245243 | A1 | 9/2013 | Jackson | |
| 2015/0133630 | A1 | 5/2015 | Suga et al. | |

FOREIGN PATENT DOCUMENTS

| | | |
|---|---|---|
| EP | 2431464 A1 | 3/2012 |
| EP | 2554672 A1 | 2/2013 |
| WO | 2012090183 A1 | 7/2012 |
| WO | 2014185802 A1 | 11/2014 |

OTHER PUBLICATIONS

Khezrian et al., Label-free electrochemical IgE aptasensor based on covalent attachment of aptamer onto multiwalled carbon nanotubes/ionic liquid/chitosan nanocomposite modified electrode, Biosensors and Bioelectronics, vol. 43, pp. 218-225. (Year: 2013).*
Benedetti et al., Plasmodium flaciparum hisitidine-rich protein II binds to actin, phosphatidylinositol 4,5-bisphosphate and erythrocyte ghosts in a pH-dependent manner and undergoes coil-to-helix transitions in anionic micelles, Molecular & Biochemical Parasitology, vol. 128, pp. 157-166. (Year: 2003).*
Ahmad et al., "Probing the Limits of Aptamer Affinity with a Microfluidic SELEX Platform," PLOS One, vol. 6, Issue 11, p. e27051, Nov. 2011.
International Search Report issued for application No. PCT/EP2017/066940 on Oct. 13, 2017.
Plow et al., "Stability of the disulfide bonds of Fibrinogen and Identification of Specific Subsets of Surface-Oriented Histidine Residues Highly Susceptible to Alkylation," Eur. J. Biochem., vol. 80, pp. 55-64, 1977.
Valery et al., "Atomic view of the histidine environment stabilizing higher-PH conformations of pH-dependent proteins," Nature Communications, vol. 6, p. 7771, Jul. 2015.

* cited by examiner

*Primary Examiner* — Dana H Shin
(74) *Attorney, Agent, or Firm* — Rouget F. Henschel; Potomac Law Group, PLLC

(57) ABSTRACT

The invention relates to a new method for obtaining aptamers directed against protein targets comprising a histidine-containing surface domain, and aptamers obtaining by said method.

9 Claims, 16 Drawing Sheets

Specification includes a Sequence Listing.

| | pmoles ssDNA | Fibrinogen | Fibrinogen affinity resin (µl) | Binding Volume (µl) | [ssDNA]binding (µM) | Incubation (min) | Washes selection buffer (SB) | Washes SB w 0.5 M NaCl |
|---|---|---|---|---|---|---|---|---|
| Round 1 | 2,000 | Transgenic Fibrinogen 66 µg (~200 pmols) | 10 | 120 | 17 | 60 | 2 x 500 µl · 5 min | - |
| | | Counter-Selection: 200 µl Fibrinogen affinity resin | | | | | | |
| Round 2 | 500 | Transgenic Fibrinogen 16.5 µg (~50 pmols) | 5 | 500 | 1 | 45 | 3 x 500 µl · 5 min | - |
| | | Counter-Selection: 200 µl Fibrinogen affinity resin | | | | | | |
| Round 3 | 500 | Transgenic Fibrinogen 16.5 µg (~50 pmols) | 5 | 1,000 | 0.5 | 30 | - | 3 x 500 µl · 5 min |
| | | Counter-Selection: 100 µl Fibrinogen affinity resin | | | | | | |
| Round 4 | 233 | 99% pure plas. Fibrinogen 16.5 µg (~50 pmols) | 5 | 400 | 0.58 | 30 | - | 3 x 500 µl · 5 min |
| | | Counter-Selection: 200 µl Fibrinogen affinity resin | | | | | | |
| Round 5 | 400 | 99% pure plas. Fibrinogen 8.25 µg (~25 pmols) | 5 | 1,500 | 0.27 | 20 | - | 4 x 500 µl · 5 min |
| | | Counter-Selection: 200 µl Fibrinogen affinity resin | | | | | | |
| Round 6 | 330 | 99.9% pure plas. Fibrinogen 6.6 µg (~20 pmols) | 5 | 1,500 | 0.22 | 15 | - | 5 x 500 µl · 5 min |
| | | Counter-Selection: 200 µl Fibrinogen affinity resin | | | | | | |
| Round 7 | 225 | 99.9% pure plas. Fibrinogen 4.95 µg (~15 pmols) | 5 | 1,500 | 0.15 | 10 | - | 5 x 500 µl · 5 min |
| | | Counter-Selection: 200 µl Fibrinogen affinity resin | | | | | | |
| Round 8 | 225 | 99.9% pure plas. Fibrinogen 4.95 µg (~15 pmols) | 5 | 1,500 | 0.15 | 10 | - | 5 x 500 µl · 5 min |

FIG. 2

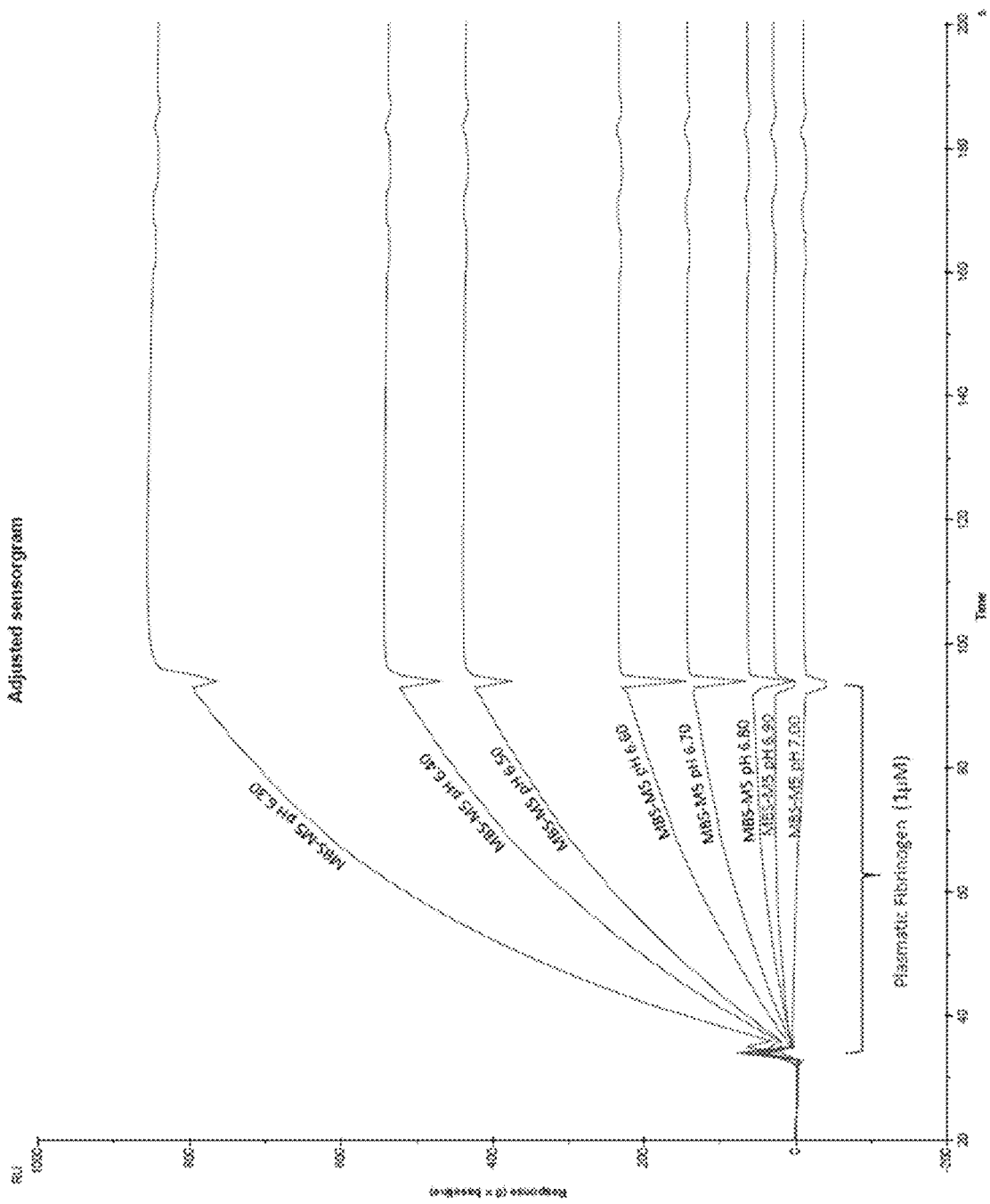

Lane 1: Plasma
Lane 2: Non retained
Lane 3: Washing
Lane 4: Fibrinogen Elution
Lane 5: Molecular weight standard

FIG. 8

| pmols ssDNA | IgG-Fc | Partitioning on | Binding Volume (μl) | [ssDNA] during binding (nM) | Binding (min) | Washes selection buffer (SB) | Washes SB w 0.5 M NaCl | Washes SB w 1 M NaCl |
|---|---|---|---|---|---|---|---|---|
| Round 1 | 2,000 | 10 μg (~200 pmols) | NC Filter | 500 | 4,000 | 60 | 2 × 10 ml 3 min | | |
| Counter-Selection: Nitrocellulose | | | | | | | | | |
| Round 2 | 468 | 2.5 μg (~50 pmols) | NC Filter | 500 | 936 | 60 | 2 × 10 ml 3 min | | |
| Counter-Selection: Nitrocellulose | | | | | | | | | |
| Round 3 | 313 | 2.5 μg (~50 pmols) | NC Filter | 627 | 500 | 45 | 3 × 10 ml 3 min | | |
| Counter-Selection: Nitrocellulose | | | | | | | | | |
| Round 4 | 428 | 2.5 μg (~50 pmols) | NC Filter | 858 | 500 | 30 | - | 4 × 10 ml 3 min | |
| Counter-Selection: Nitrocellulose | | | | | | | | | |
| Round 5 | 375 | 2.5 μg (~50 pmols) | NC Filter | 1,252 | 300 | 20 | - | 5 × 10 ml 3 min | |
| Counter-Selection: Nitrocellulose | | | | | | | | | |
| Round 6 | 300 | 1.5 μg (~30 pmols) | NC Filter | 1,500 | 200 | 15 | - | 5 × 10 ml 3 min | |
| Counter-Selection: Nitrocellulose | | | | | | | | | |
| Round 7 | 450 | 1.5 μg (~30 pmols) | NC Filter | 3,000 | 150 | 10 | - | | 5 × 10 ml 3 min |
| Counter-Selection: Nitrocellulose | | | | | | | | | |
| Round 8 | 450 | 1.5 μg (~30 pmols) | NC Filter | 3,000 | 150 | 5 | - | | 6 × 10 ml 3 min |

ANTI-FIBRINOGEN APTAMERS

FIELD OF THE INVENTION

The instant patent application relates to improved methods for obtaining aptamers directed against proteins such as fibrinogen and immunoglobulins.

BACKGROUND OF THE INVENTION

Aptamers are synthetic, single-stranded polynucleotides having unique 3-D structures allowing them to bind specifically to other target molecules. Aptamers generally exhibit high affinity for their target with Kd values in the low nanomolar to picomolar range.

Aptamers are routinely identified through process called Systematic Evolution of Ligands by Exponential enrichment (SELEX). All SELEX-based processes comprise common sequential steps: The processes begin by the generation of a large and random library of about $10^{12}$ to $10^{15}$ DNA or RNA molecules. The random library is incubated directly with the target, whereby certain oligonucleotides of the library specifically bind to the target. The target-binding oligonucleotides are separated from nonbinding oligonucleotides, eluted and amplified by PCR (for DNA SELEX) or RT-PCR (for RNA SELEX) so as to generate a new and enriched pool of selected oligonucleotides. Iterative rounds of selection and amplification are performed until the target-interacting sequences dominate the population. Typically from 6 to 18 iterative cycles of selection and amplification are needed to obtain aptamers with suitable affinity to the target (Proske, Appl Microbiol. Biotechonol, 2005, 69:367-374, Stoltenburg et al., Biomolecular Engineering, 2007, 24, 381-403). Additional steps can be introduced into each round of the process in order to control the binding properties of the oligonucleotides. For instance, negative selection steps can be introduced in order to remove aptamers which cross-react with another protein or in order to direct the selection to aptamers binding to a specific epitope of the target. Over the last decade, SELEX technology enabled the identification of aptamers directed against a wide variety of targets such as small molecules, peptides and proteins, including cell membranes proteins. Despite SELEX processes are all based on the same principle, there is no standardized SELEX protocol which would work for any target. The SELEX design and the conditions to use, in particular in the selection step, depend on the target, the composition of the starting library, and the desired features sought for the aptamers in terms of affinity, selectivity and potential application.

As of today, the identification of aptamers directed against certain protein targets remain a real challenge. The success rate of basic SELEX is less than 30%. Indeed, certain proteins, such as fibrinogen or immunoglobulin, are resistant to SELEX process, whereby the identification of aptamers directed against these proteins is very difficult and even impossible, starting from natural oligonucleotide libraries or 2'-O-modified RNA libraries.

The limited chemical diversity of oligonucleotide libraries has been suspected as the main cause explaining the low rate of success of basic SELEX. Gold and coll. thus suggest introducing chemically-modified nucleotides comprising functional groups which mimic side-chains of amino acids. They built chemically-modified oligonucleotides comprising 5-modified deoxyuridine with hydrophobic groups such as alkyl chains and aromatic groups. The use of such libraries made a dramatic difference in terms of success rate of SELEX: Gold and coll. enabled to obtain success rates of about 80%, and identified chemically-modified aptamers with Kd of the nM range directed against different resistant-SELEX proteins. These aptamers called SOMAmers (for Slow Off-rate Modified Aptamers) are characterized by high koff. The interactions between the SOMAmers and their target are less polar and more hydrophobic as compared to conventional aptamers (Rohloff et al., Molecular Therapy-Nucleic Acids, 2014, 3, e201).

However, despite the high rate of success, 5-modified deoxyuridine libraries have several drawbacks. There is no universal chemically modified oligonucleotide library which enables to identify appropriate SOMAmers for any target. Indeed, the chemically modified library to use for a given target (i.e. the type of functional moiety to introduce on the backbone of nucleotides) cannot be predicted a priori, whereby for a given target, it may be necessary to randomly perform several SELEX processes from several different starting libraries in order to identify the appropriate starting library to use. Moreover, such SELEX technology is more demanding and more costly to implement. At last, SOMAmers are not suitable to be used as affinity ligands in purification because of their binding property that are not likely to allow elution of the protein target in mild and selective elution conditions.

There is thus a need for an alternative SELEX process enabling to identify aptamers directed against SELEX-resistant proteins and which would be suitable for use in purification.

SUMMARY OF THE INVENTION

The invention relates to a method for obtaining an aptamer against a protein target comprising a histidine-containing surface domain, said method comprising:
  a) contacting the protein target with a candidate mixture of nucleic acids at a pH promoting the formation of positive charge on the histidine-containing surface domain of said protein target,
  b) recovering nucleic acids which bind to the protein target, while removing unbound nucleic acids,
  c) amplifying the nucleic acids obtained in step (b) to yield to a candidate mixture of nucleic acids with increased affinity to the protein target, and
  d) repeating steps (a), (b), (c) until obtaining one or several aptamers against the protein target of interest.

In some embodiments, the pH in step a) is less than 7.0, preferably from 5.0 to 6.9. In some other or additional embodiments, the pH in step a) is selected so that the electrostatic surface potential of a histidine-containing surface domain of the protein target is positive.

In some other embodiments, the pH of step (a) is determined by obtaining surface electrostatic potential maps at different pH and selecting a pH which enables to obtain a positive surface potential on at least one histidine-containing surface domain of the protein target and which is included in the stability range of the protein target.

The protein target may comprise at least one of the following feature:
  the protein target has an isoelectric point (pI) of less than 7.5, preferably less than 7.0 and/or
  the protein target is devoid of any surface domain with positive electrostatic potential at a pH of more than 7.0.

In some embodiments, the protein target is selected from the group consisting of fibrinogen, immunoglobulin, Fc fragment, and variants thereof.

In step a), the candidate mixture may consist of a multitude of single-stranded DNAs.

In some further embodiments, step b) comprises the sub-steps of
    separating the complex formed in step (a) from unbound nucleic acids, and
    releasing the nucleic acids from the complex, wherein the dissociation of the complex between the bound nucleic acids and the protein target is performed by increasing the pH at a value higher than that used in step a), preferably of a ΔpH of at least 0.8.

In certain embodiments, the method of the invention may comprise the steps of
    i. sequencing an aptamer obtained in step (c),
    ii. optionally optimizing the sequence of said aptamer, and
    iii. producing the aptamer, preferably by chemical synthesis.

In another aspect, the invention relates to an aptamer obtainable or obtained by the method as defined above. Preferably, the aptamer binds to a protein target comprising a histidine-containing surface domain in a pH dependent-manner. For instance, the aptamer of the invention binds to the protein target at an acidic pH, preferably selected from 5.0 to 6.5, but does not bind to the protein target at a pH of more than 7.0.

The invention also relates to an affinity ligand which comprises an aptamer of the invention and at least one moiety for immobilization onto a support. An additional object of the invention is an affinity support comprising thereon a plurality of aptamers or a plurality of affinity ligands as defined above.

An additional object of the invention is a method for obtaining an aptamer against a protein target said method comprising:
    (i) determining a pH value promoting positive charges in at least one surface domain of the protein target,
    (a) contacting the protein target with a candidate mixture of nucleic acids at the pH determined in step (i) in conditions favourable for binding of the protein target with nucleic acids having affinity for said targets,
    (b) recovering nucleic acids which bind to the protein target, while removing unbound nucleic acids,
    (c) amplifying the nucleic acids obtained in step (b) to yield to a candidate mixture of nucleic acids with increased affinity to the protein target, and
    (d) repeating steps (a), (b), (c) until obtaining one or several aptamers against the protein target of interest.

In some embodiments, said method of claim comprises the steps of:
    determining the presence of a histidine-containing surface domain in the protein target, and
    if said domain is present, determining a pH value promoting positive charges, preferably enabling to obtain a local positive surface electrostatic potential, in said histidine-containing surface domain.

BRIEF DESCRIPTION OF THE DRAWINGS

FIG. 2 shows the protocol of the SELEX according to the invention used to identify aptamers directed against human fibrinogen.

FIGS. 3A-3D and 4A-4B show the binding properties of some aptamers directed against human fibrinogen obtained by the method of the invention:

FIG. 3A shows the SPR binding curves of human plasma fibrinogen present at a concentration from 125 nM to 1000 nM on SEQ ID NO: 3 (the core sequence of SEQ ID NO:1) immobilized on a chip. Each solution of human plasma fibrinogen was injected at pH 6.3 whereby a complex was formed in a dose-dependent manner as evidenced by the increase of the signals depending on the concentration of fibrinogen. The injection of a buffer solution at pH 6.3 comprising 0.5 M NaCl did not significantly induce the elution of human plasma fibrinogen. Fibrinogen was then released from the complex by an elution buffer at pH 7.40. The solid support was then regenerated by injecting a solution of NaOH at 50 mM. X-axis: time in s. Y-axis: SPR response in arbitrary scale.

FIG. 3B shows the SPR binding curves of transgenic fibrinogen present at a concentration from 125 nM to 1000 nM on SEQ ID NO: 3 (the core sequence of SEQ ID NO:1) immobilized on a chip. Each solution of transgenic fibrinogen was injected at pH 6.3 whereby a complex was formed in a dose-dependent manner as evidenced by the increase of the signals depending on the concentration of fibrinogen. The injection of a buffer solution at pH 6.3 comprising 0.5 M NaCl did not significantly induce the elution of transgenic fibrinogen. Fibrinogen was then released from the complex by an elution buffer at pH 7.40. The solid support was then regenerated by injecting a solution of NaOH at 50 mM. X-axis: time in s. Y-axis: SPR response in arbitrary scale FIG. 3C shows the SPR binding curves of human plasma fibrinogen present at a concentration from 125 nM to 1000 nM on SEQ ID NO: 4 (the core sequence of SEQ ID NO:2) immobilized on a chip. Each solution of human plasma fibrinogen was injected at pH 6.3 whereby a complex was formed in a dose-dependent manner as evidenced by the increase of the signals depending on the concentration of fibrinogen. The injection of a buffer solution at pH 6.3 comprising 1 M NaCl did not considerably induce the elution of human plasma fibrinogen. Fibrinogen was then released from the complex by an elution buffer at pH 7.40 and containing MgCl2 at 2M. The solid support was then regenerated by injecting a solution of NaOH at 50 mM. X-axis: time in s. Y-axis: SPR response in arbitrary scale.

FIG. 3D shows the SPR binding curves of transgenic fibrinogen present at a concentration from 125 nM to 1000 nM on SEQ ID NO: 4 (the core sequence of SEQ ID NO:2) immobilized on a chip. Each solution of transgenic fibrinogen was injected at pH 6.3 whereby a complex was formed in a dose-dependent manner as evidenced by the increase of the signals depending on the concentration of fibrinogen. The injection of a buffer solution at pH 6.3 comprising 1 M NaCl did not considerably induce the elution of transgenic fibrinogen. Fibrinogen was then released from the complex by an elution buffer at pH 7.40 and containing MgCl2 at 2M. The solid support was then regenerated by injecting a solution of NaOH at 50 mM. X-axis: time in s. Y-axis: SPR response in arbitrary scale.

FIG. 4A shows SPR sensograms illustrating the pH dependency of binding of fibrinogen to immobilised aptamer SEQ ID NO:3 (the core sequence of SEQ ID NO:1).

Plasmatic Fibrinogen is injected at different pH, after sample injection a running buffer at pH 6.30 is passed over the flow cell in every run. The highest binding level is obtained for pH 6.30. The binding level decreases when pH increases. X-axis: time in s. Y-axis: SPR response in arbitrary scale.

Figure 1A:
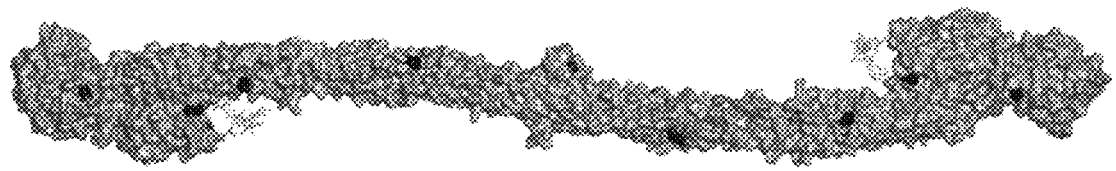
FIG. 1A shows the three-dimensional structure of human fibrinogen. The surface histidine are indicated in dark. Eighteen histidines are distributed over the surface of homodimeric fibrinogen with an inter-histidine distance between 10-65 Angstrom.
Figure 1B:
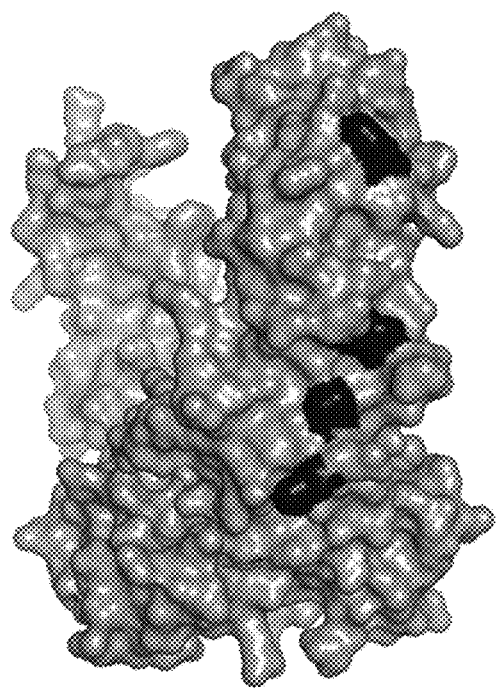
FIG. 1B shows the three-dimensional structure of homodimeric Fc of human IgG. The surface histidines of one of the monomers are shown in dark. There are four surface histidines per monomer. Three surface histidines (H433, H435, H310) are positioned in a close linear arrangement with an inter-histidine distance of 10 Angstrom. The fourth histidine is at a distance of 22 Angstrom from the closest of the tree others histidines. The surface histidines of the second monomer are on the backside.
Figure 3A:
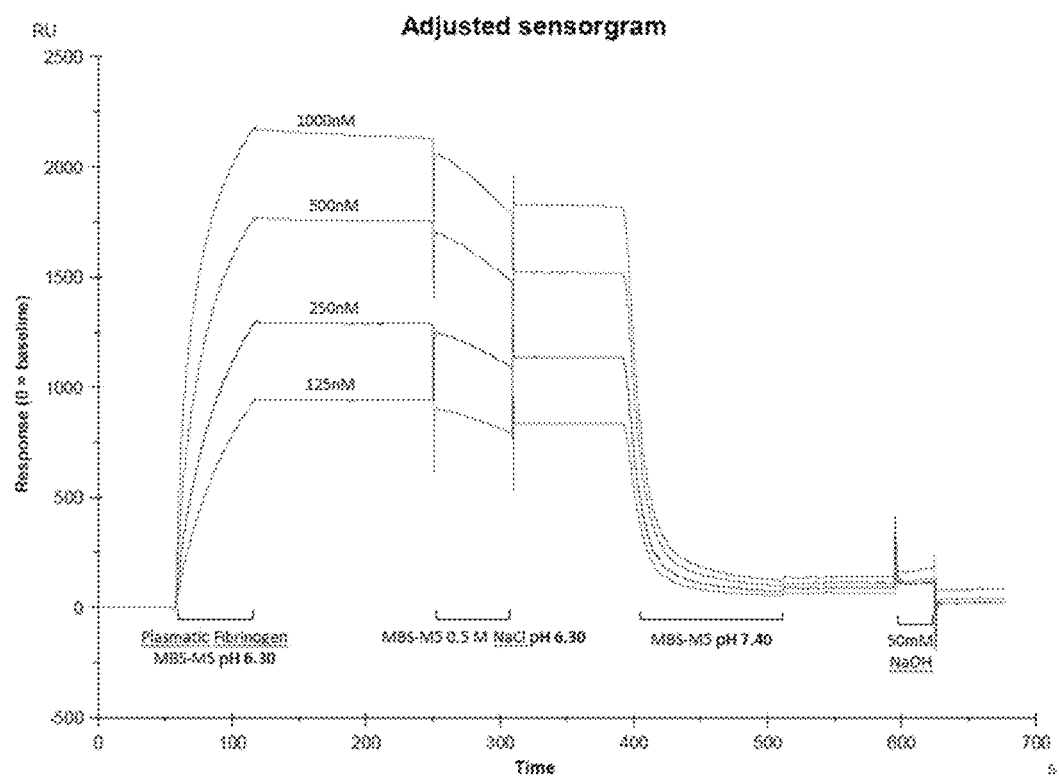
Figure 3B:
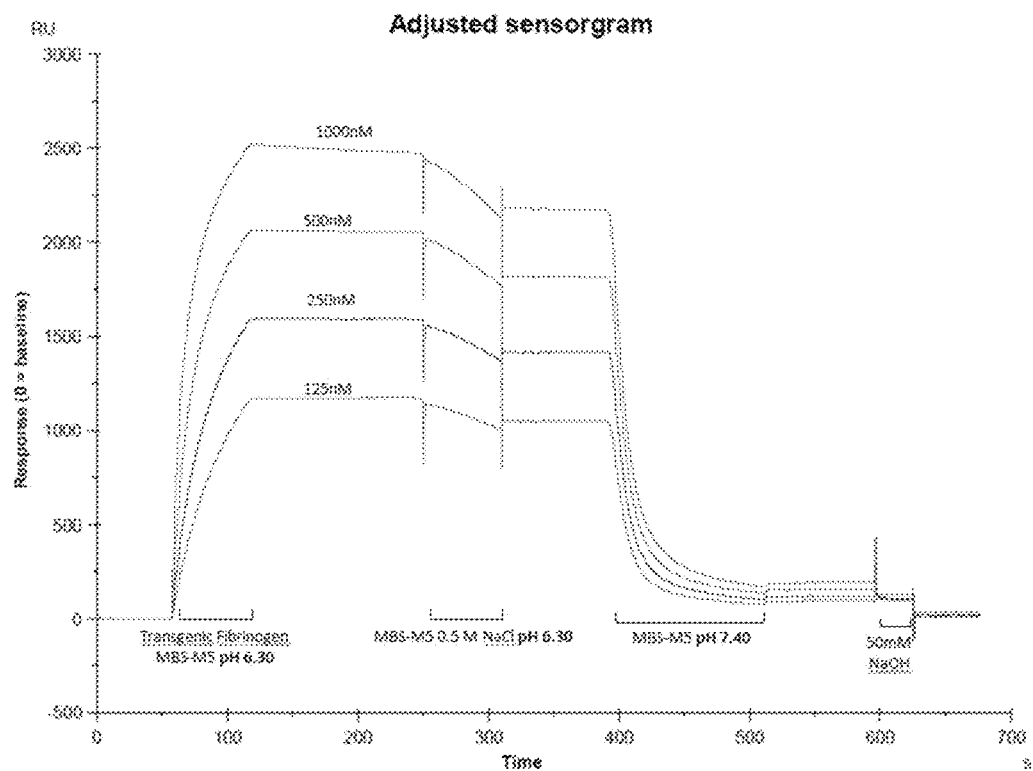
Figure 3C:
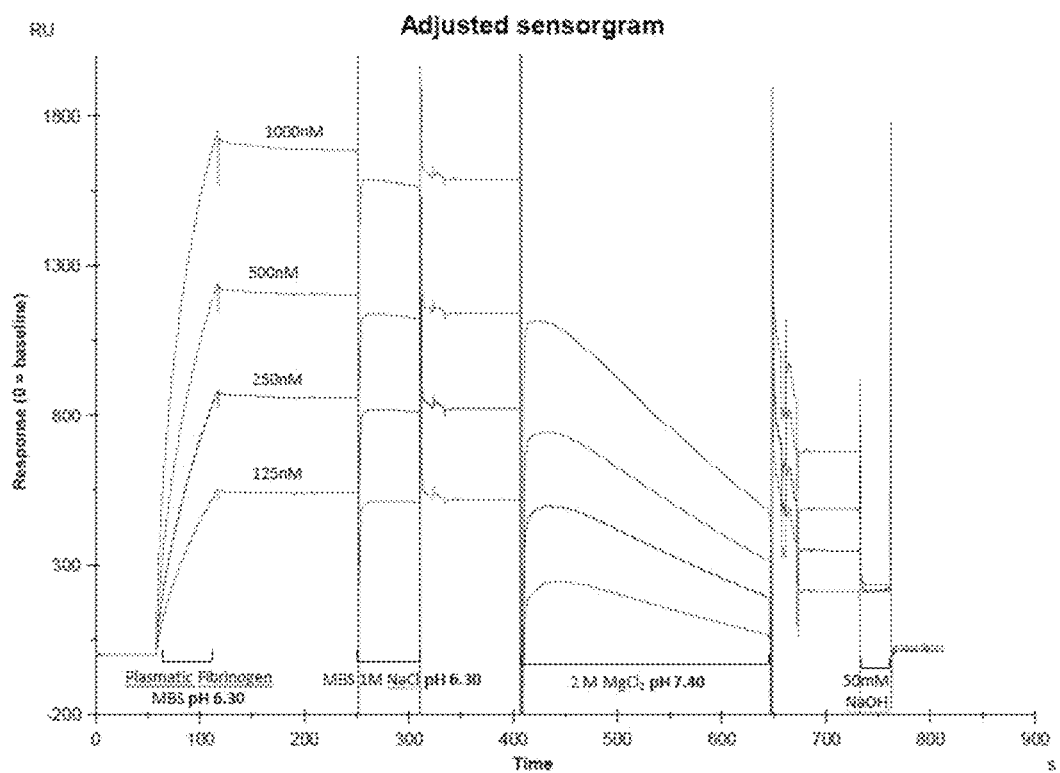
Figure 3D:
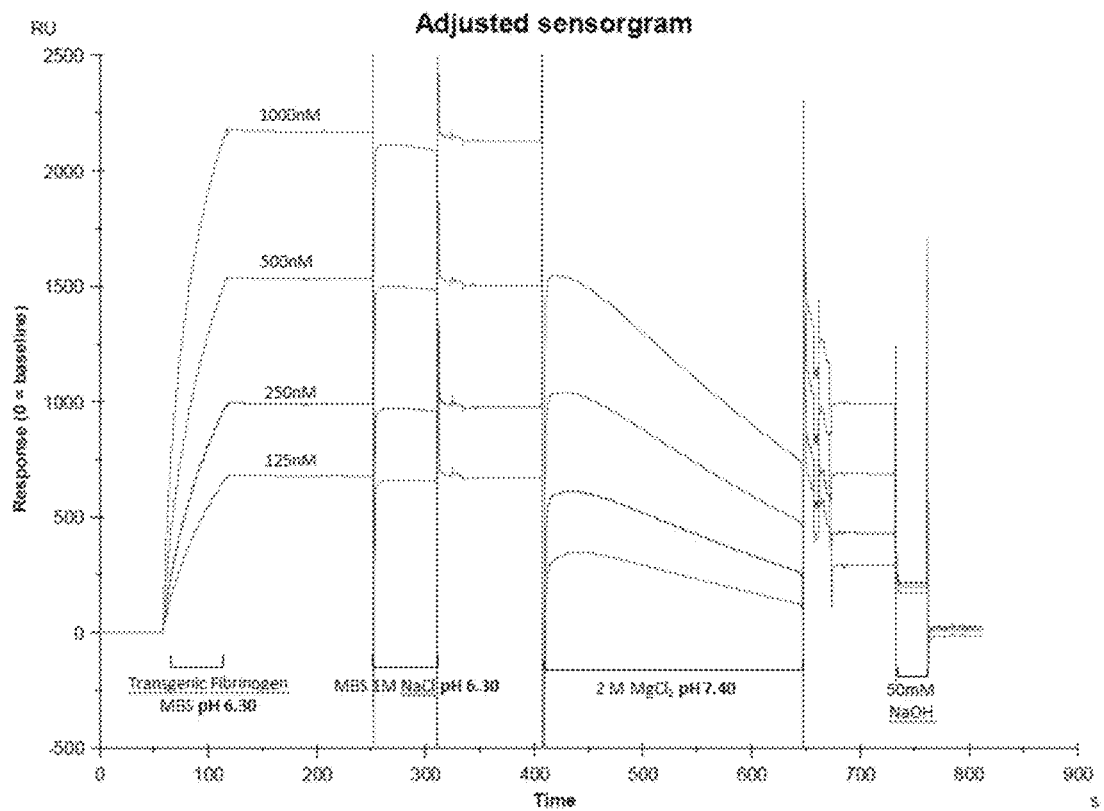
Figure 4B:
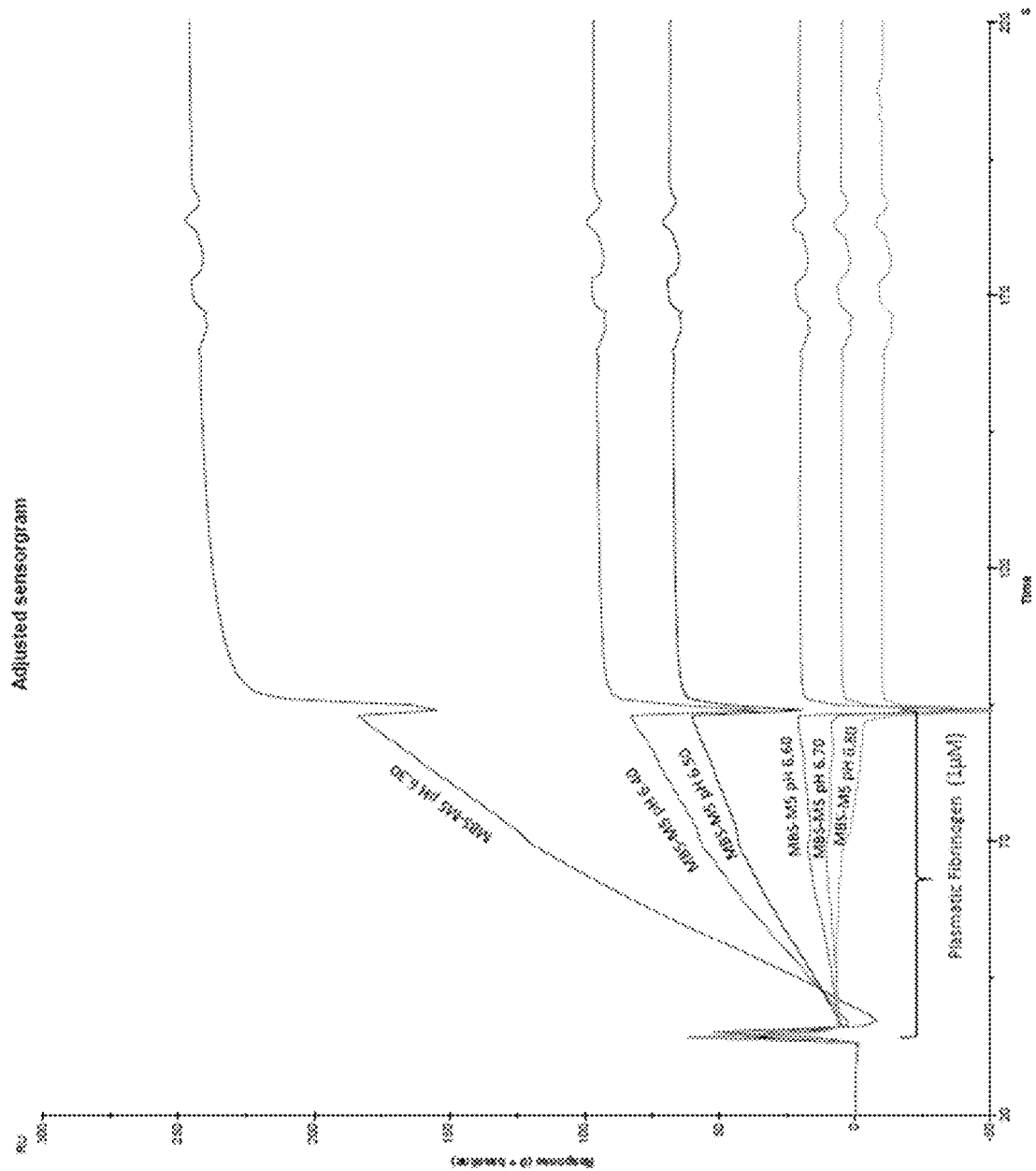

FIG. 4B shows SPR sensograms illustrating the pH dependency of binding affinity of aptamer of SEQ ID NO: 4 (the core sequence of SEQ ID NO:2) to human plasma fibrinogen. No binding is observed for pH higher than 6.8. X-axis: time in s. Y-axis: SPR response in arbitrary scale.

Figure 5A:
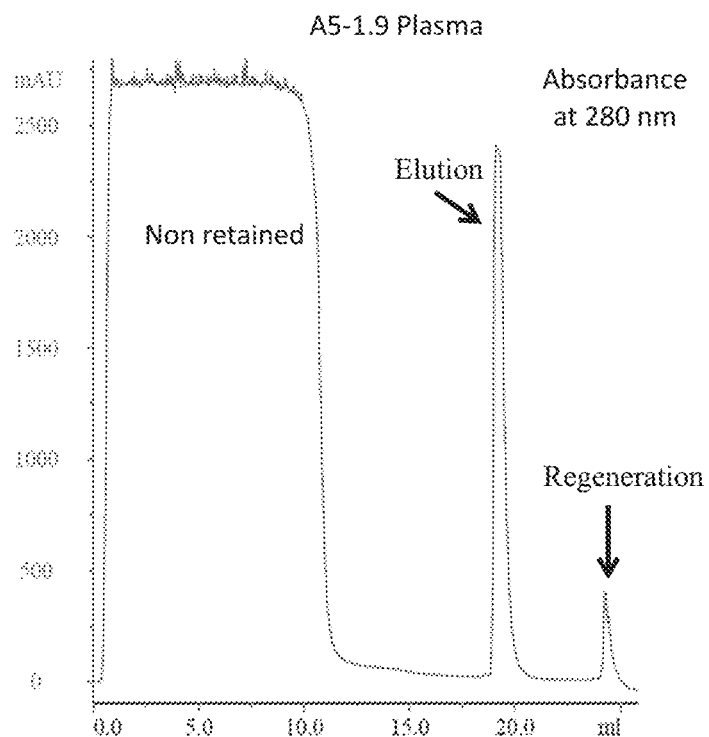
Figure 5B:
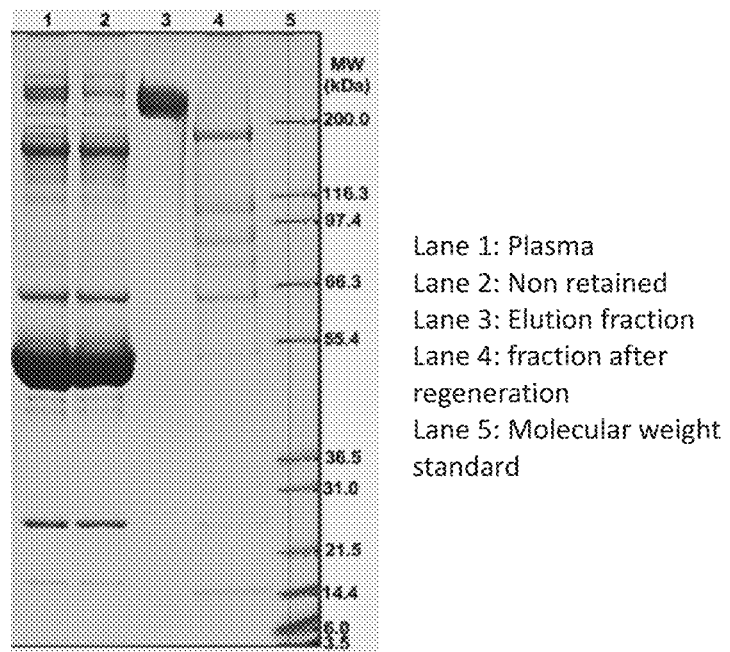

FIG. 5A shows the chromatographic profile for the purification of fibrinogen on an affinity support grafted with aptamer of SEQ ID NO:3. Y-axis: absorbance at 280 nm. X-axis: in mL FIG. 5B shows the picture of the electrophoresis gels after coomassie blue staining in non-reduced conditions. From left to right: 1: plasma, 2: fraction from the plasma which was not retained on the stationary phase, 3: elution fraction containing fibrinogen obtained from the chromatography of plasma, 4: fraction obtained after regeneration of the stationary support, and 5: molecular weight markers. The purity of the elution fraction for fibrinogen was more than 95% as compared to the total amount of proteins contained in the fraction. The affinity support used in chromatography was grafted with aptamers of SEQ ID NO:3.

Figure 6A:
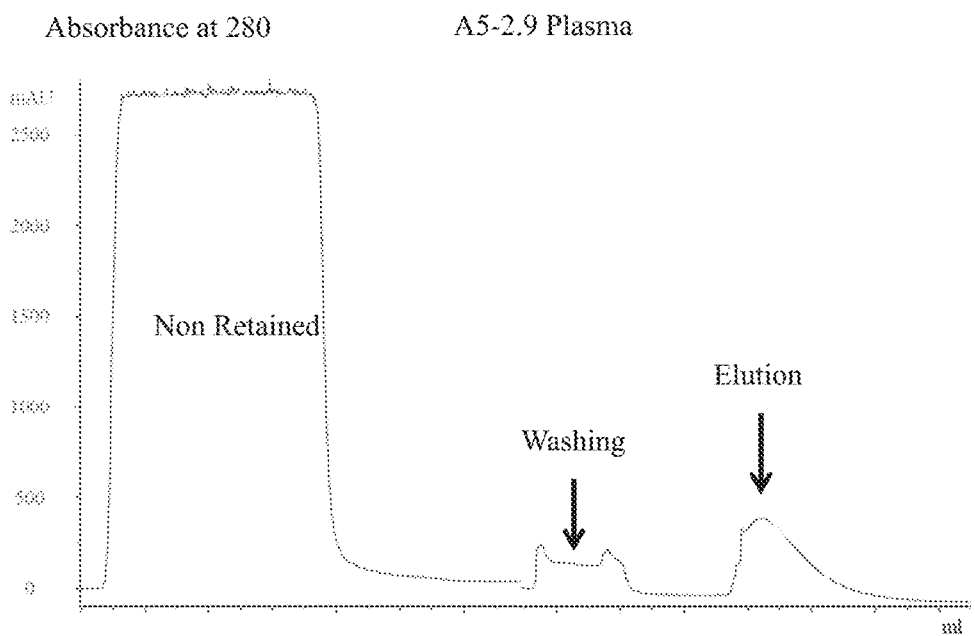
Figure 6B:
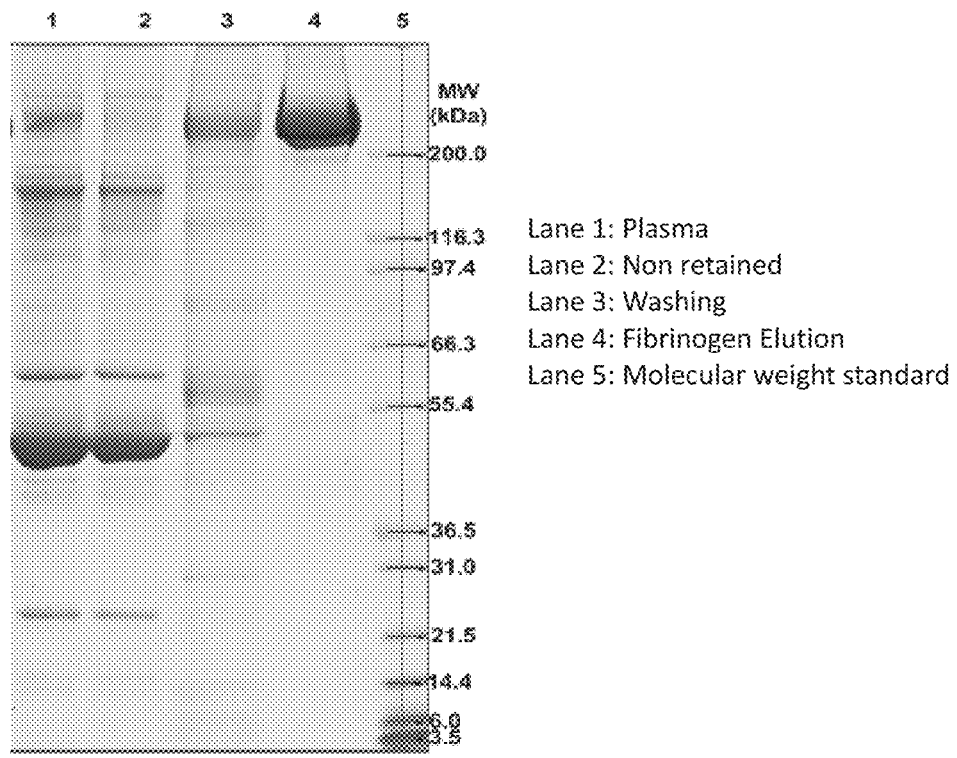

FIG. 6A shows the chromatographic profile for the purification of fibrinogen from plasma on an affinity support grafted with aptamer of SEQ ID NO:4. Y-axis: absorbance at 280 nm. X-axis: in mL FIG. 6B shows the picture of the electrophoresis gels after coomassie blue staining in non-reduced conditions. From left to right: 1: plasma, 2: fraction from the plasma which was not retained on the stationary phase, 3: fraction obtained after washing of the stationary support, 4: elution fraction containing fibrinogen obtained from the chromatography of plasma, and 5: molecular weight markers. The purity of the elution fraction for fibrinogen was of least 95% as compared to the total amount of proteins contained in the fraction. The affinity support used in chromatography was grafted with aptamers of SEQ ID NO:4.

Figure 7A:
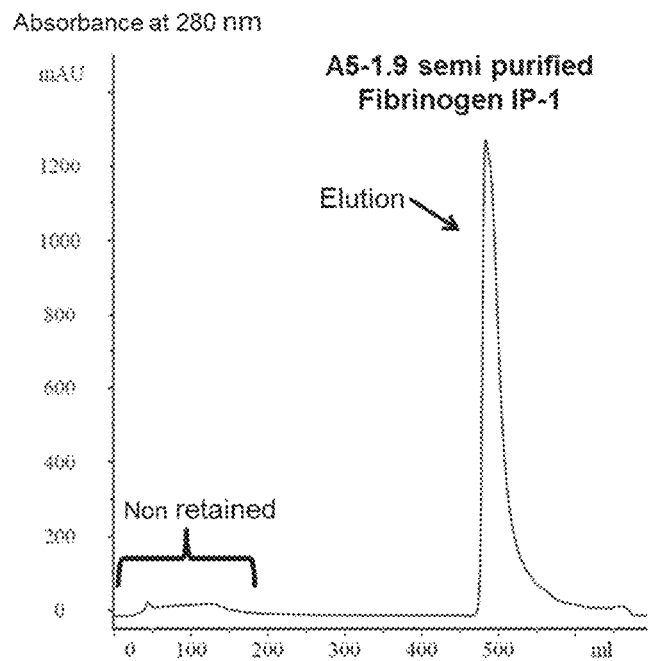
Figure 7B:
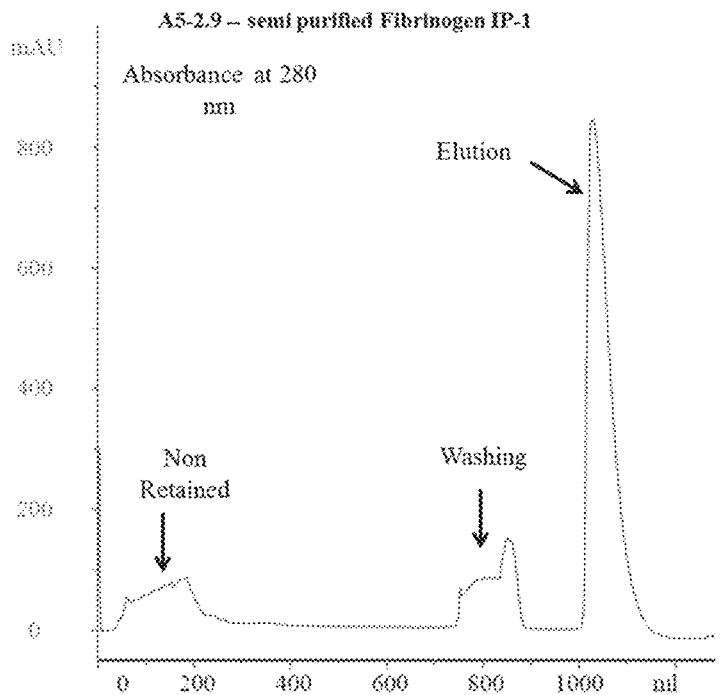

FIG. 7A shows the chromatographic profile obtained for the purification of semi-purified fibrinogen on an affinity support grafted with aptamer of SEQ ID NO:3. Y-axis: absorbance at 280 nm. X-axis: in mL FIG. 7B shows the chromatographic profile obtained for the purification of semi-purified fibrinogen on an affinity support grafted with aptamer of SEQ ID NO:4. Y-axis: absorbance at 280 nm. X-axis: in mL.

Figure 7C:
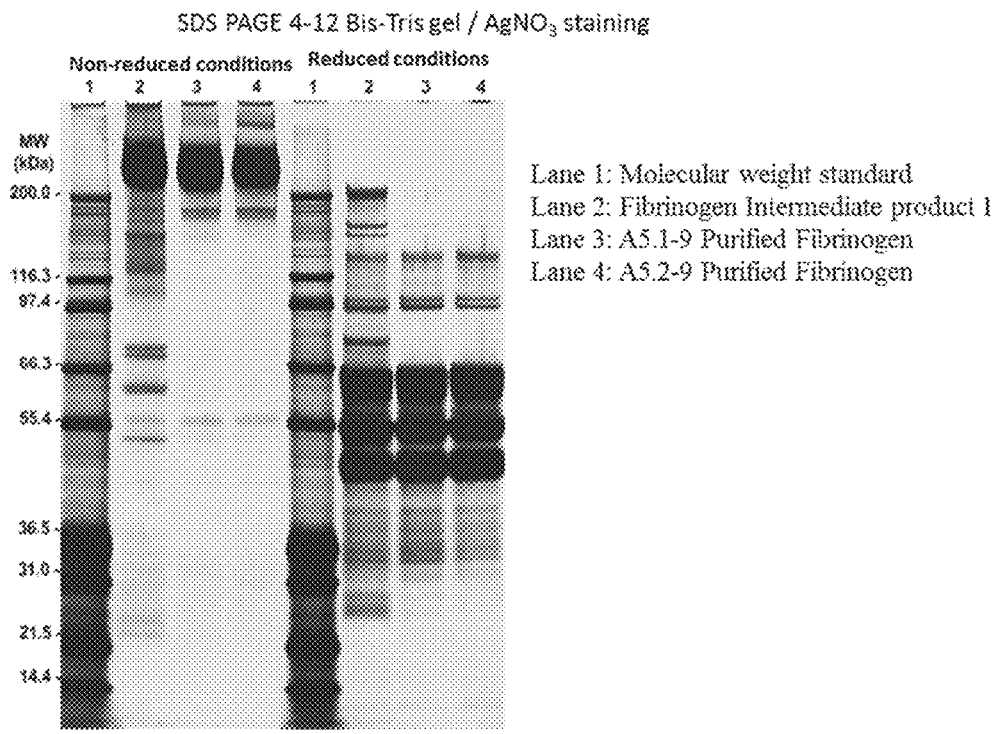

FIG. 7C shows the analysis of the fractions by SDS-PAGE in reduced and non-reduced conditions, with AgNO3 staining, of the elution fractions obtained by purification of intermediate fibrinogen on the affinity supports. Lane 1: molecular weight standard. Lane 2: Fibrinogen intermediate (starting material), Lane 3: Elution fraction obtained with affinity support n° 1 (aptamers of SEQ ID NO:3), Lane 4: Elution fraction obtained with affinity support n° 2 (aptamers of SEQ ID NO:4)

Figure 7D:
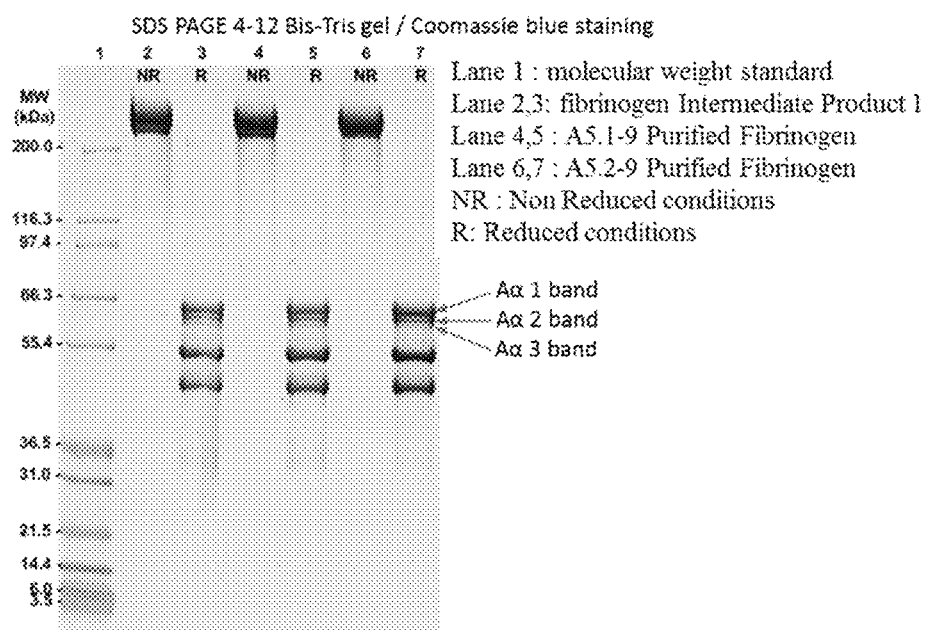

FIG. 7D shows the analysis of the fractions by SDS-PAGE in reduced and non-reduced conditions, with coomassie staining, of the elution fractions obtained by purification of intermediate fibrinogen on the affinity supports. Lane 1: molecular weight standard. Lane 2,3: Fibrinogen intermediate (starting material), Lane 4,5: Elution fraction obtained with affinity support n° 1 (aptamers of SEQ ID NO:3), Lane 6,7: Elution fraction obtained with affinity support n° 2 (aptamers of SEQ ID NO:4). NR: non reduced. R: Reduced.

FIG. 8 shows the SELEX protocol used to identify aptamers directed against Fc fragment of human IgG.

Figure 9A:
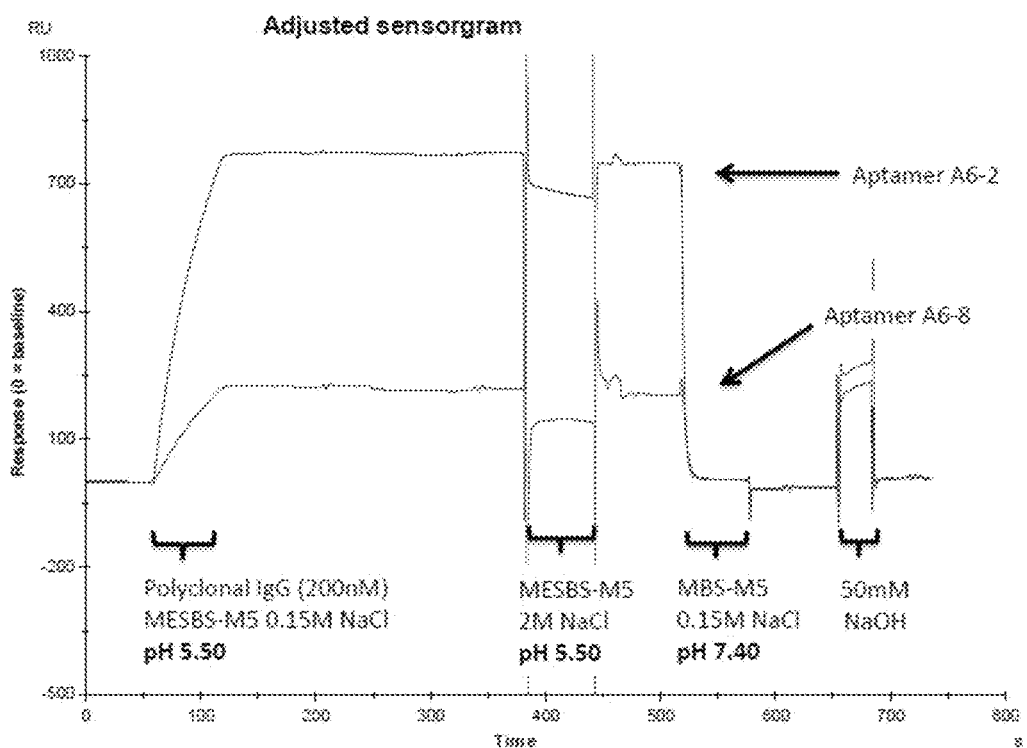
Figure 9B:
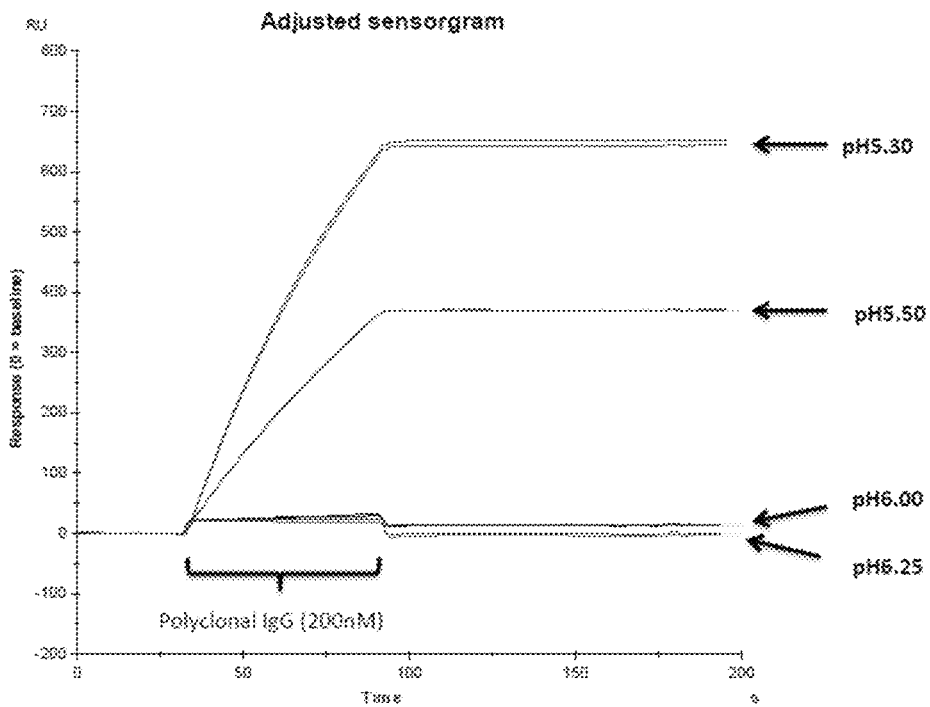

FIGS. 9A-9B show the binding properties of some aptamers directed against human Fc fragment obtained by the method of the invention:

FIG. 9A shows the binding curves of human polyclonal IgG (sensorgram) for aptamers of SEQ ID NO:5 (A6-2) and SEQ ID NO:6 (A6-8) immobilized on a sensor chip, obtained by SPR technology. Purified (>95%) human polyclonal IgG (200 nM) was injected at pH 5.50, whereby a complex was formed as evidenced by the increase of the signal. The injection of a buffer solution at pH 5.50 comprising 2M NaCl did not significantly induce the elution of human polyclonal IgG. Human polyclonal IgG was then released from the complex by an elution buffer at pH 7.40. The solid support was then regenerated by injecting a solution of NaOH at 50 mM. X-axis: time in s. Y-axis: SPR response in arbitrary scale FIG. 9B shows SPR sensograms illustrating the pH dependency of binding of polyclonal IgG to immobilised aptamer A6-2. Polyclonal IgG is injected at different pH (in duplicates), after sample injection a running buffer at pH 5.50 is passed over the flow cell in every run. The highest binding level is obtained for pH 5.30. The binding level decreases when pH increases. X-axis: time in s. Y-axis: SPR response in arbitrary scale.

Figure 10A:
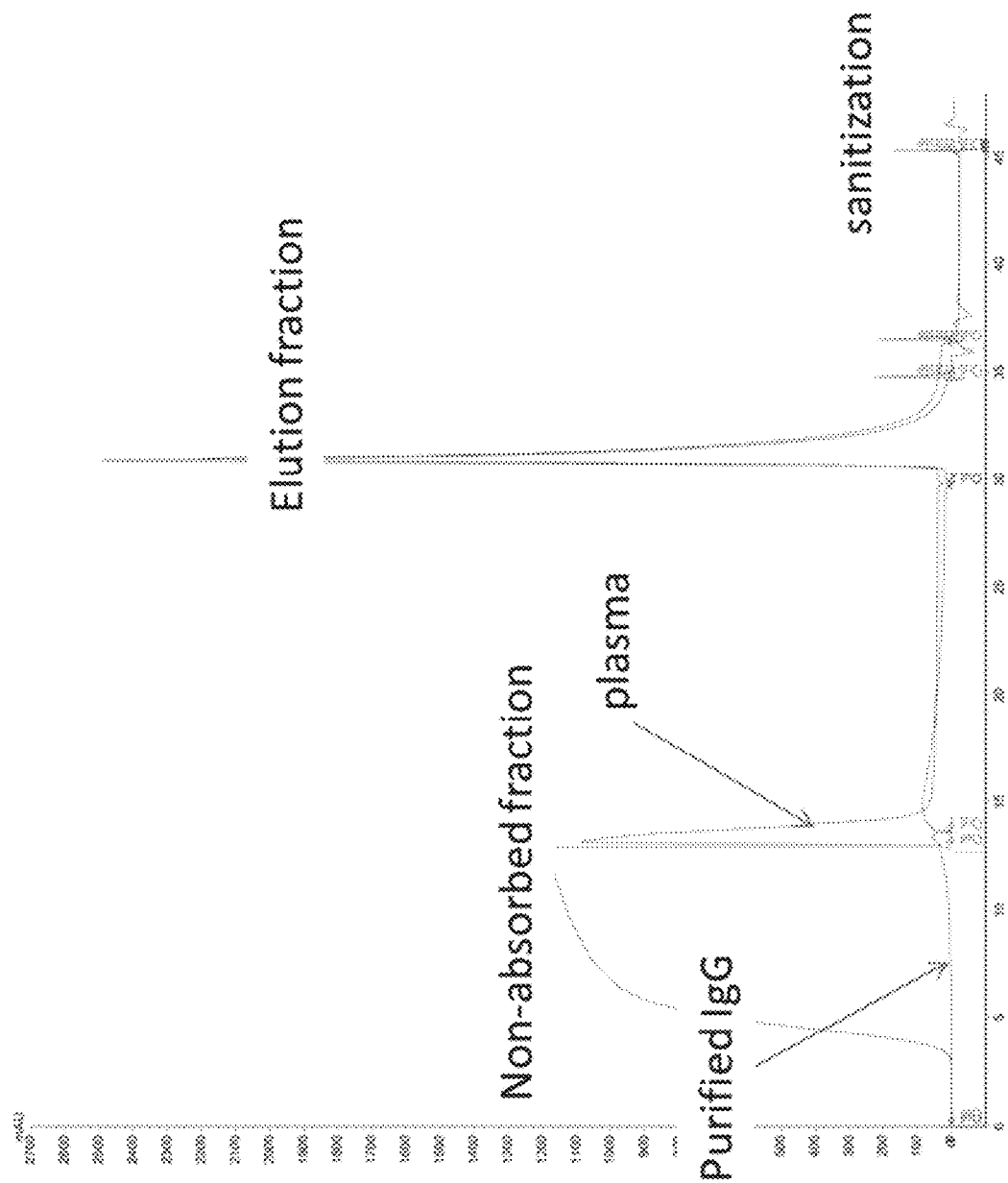
Figure 10B:
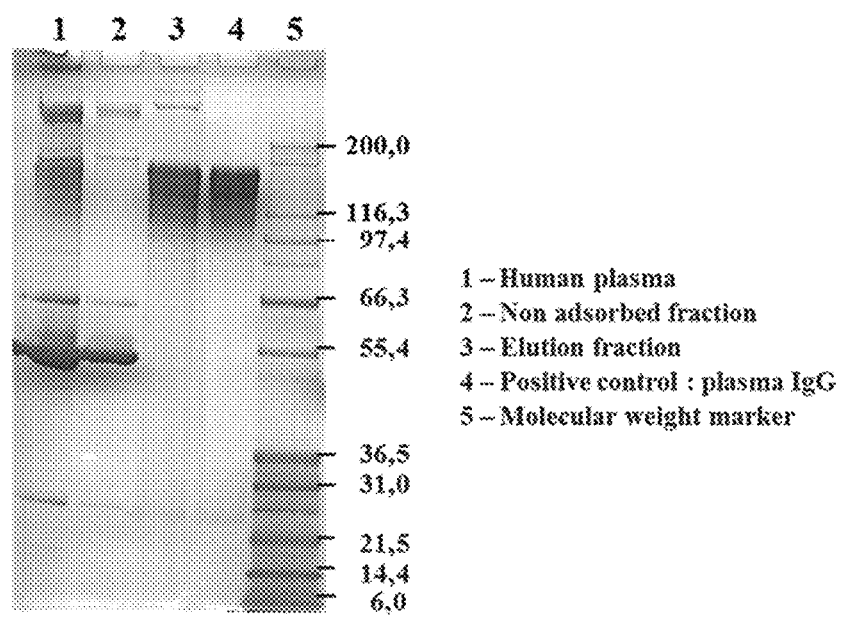

FIG. 10A shows the chromatographic profiles for plasma and pre-purified IgG on an affinity support grafted with aptamer of SEQ ID NO:5. Y-axis: absorbance at 280 nm. X-axis: in mL FIG. 10B shows the picture of the electrophoresis gel after coomassie blue staining. From left to right: 1: human plasma, 2: fraction from the plasma which was not retained on the stationary phase, 3: elution fraction containing IgGs obtained from the chromatography of plasma, 4: positive control (plasma IgG) and 5: molecular weight markers.

Figure 11A:
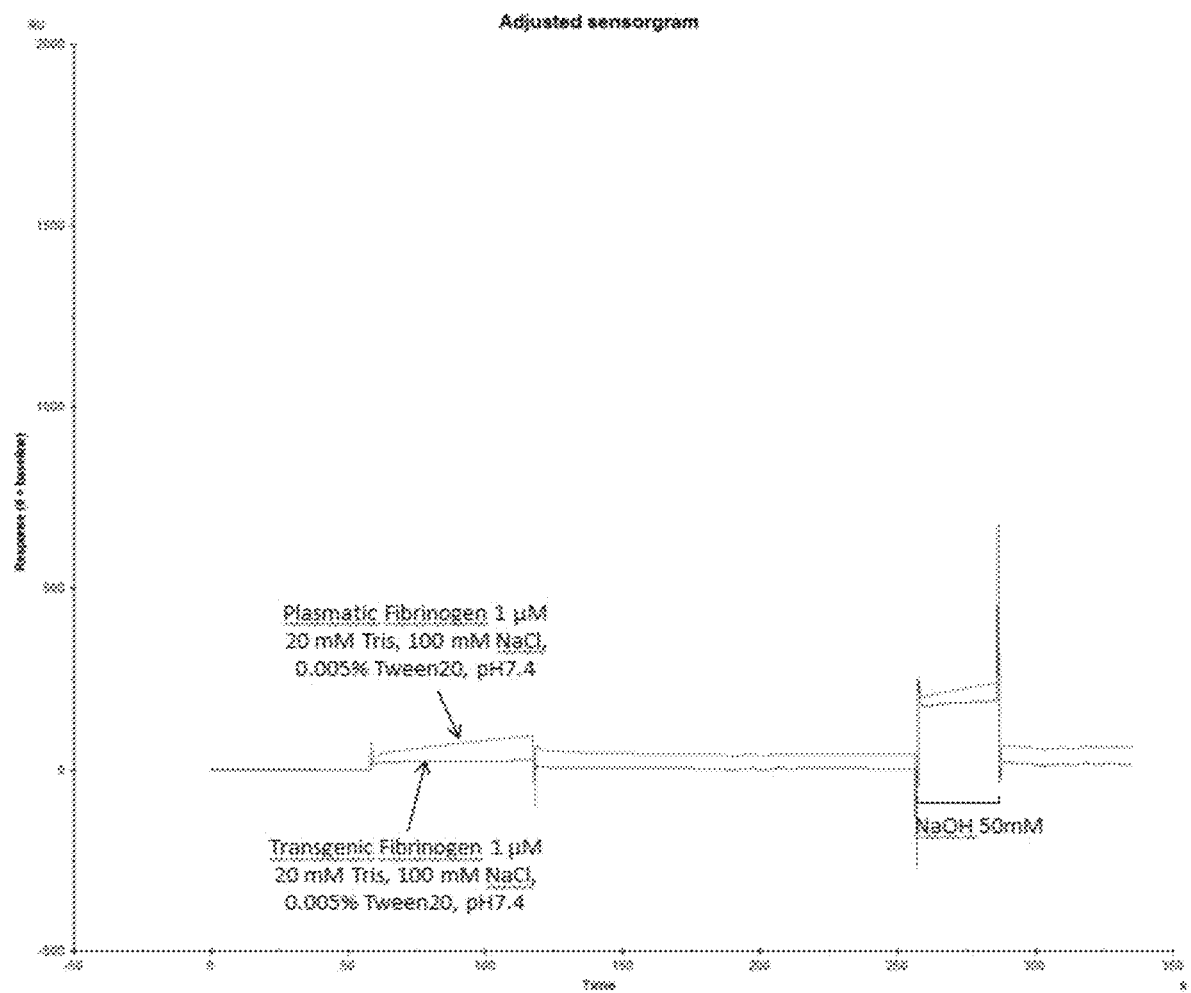

FIG. 11A shows the binding curves of human plasmatic and transgenic fibrinogen (sensorgram) for an aptamer from Base Pair Biotechnologies (reference 6F01 oligo #370) immobilized on a sensor chip, obtained by SPR technology. Human plasmatic and transgenic fibrinogen (1000 nM) was injected at pH 7.40 using the Base Pair Biotechnologies recommended buffer. Very low binding levels were observed for human plasmatic and transgenic fibrinogen. The solid support was then regenerated by injecting a solution of NaOH at 50 mM. X-axis: time in s. Y-axis: SPR response in arbitrary scale.

Figure 11B:
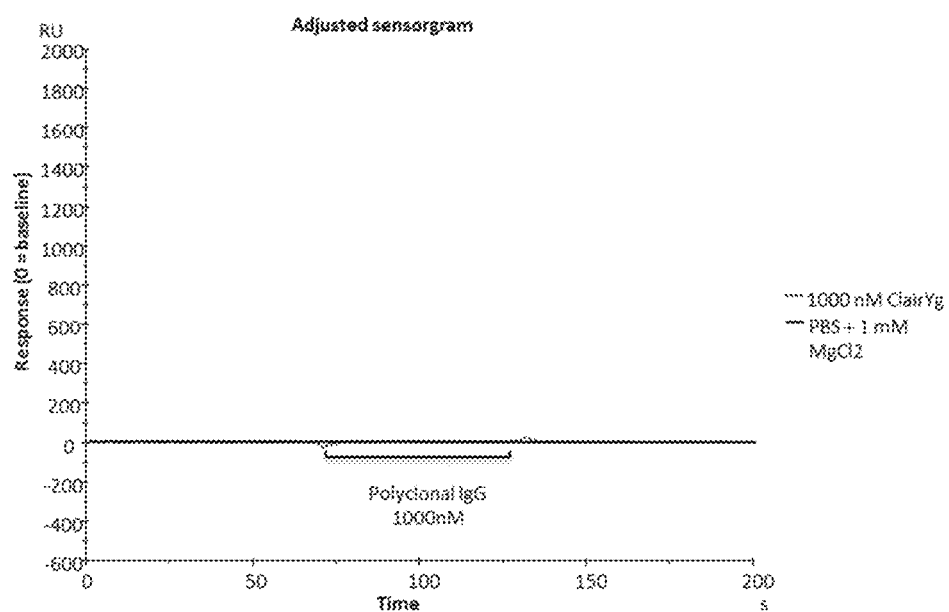

FIG. 11B shows the binding curve of purified plasma IgG (sensorgram) for aptamer ATW0018 from Base Pair technologies using the binding buffer recommended by the manufacturer, namely PBS buffer containing 1 mM $MgCl_2$. No binding was observed. X-axis: time in s. Y-axis: SPR response in arbitrary scale.

REMARKS

MBS buffer refers to 50 mM MOPS/150 mM NaCl
MBS 1M NaCl buffer refers to 50 mM MOPS/1M NaCl
MBS-M5 buffer refers to: 50 mM MOPS/150 mM NaCl/5 mM $MgCl_2$
MBS-M5 0.5M NaCl buffer refers to 50 mM MOPS pH 6.30/0.5M NaCl/5 mM MgCl2

DETAILED DESCRIPTION OF THE INVENTION

The success rate of SELEX processes from standard oligonucleotide libraries is less than 30%, whereby it may be impossible to obtain aptamers directed to certain proteins having unfavourable properties which might preclude strong interactions with aptamers. The use of chemically modified libraries as described in Rohloff et al., (see supra) has increased the success rate, but this method has several drawbacks. This method is time-consuming, expensive and difficult to implement. Moreover the use of such starting libraries leads to aptamers having binding properties which may preclude their use as affinity ligands in purification technology such as chromatography.

In that context, the Applicant performed extensive researches to develop a new method for obtaining aptamers directed against "SELEX-resistant" proteins.

The Applicant conceived a new SELEX process which enables to obtain aptamers displaying high binding affinity for "SELEX-resistant" proteins, and which may be used as affinity ligands in purification process. This new SELEX process is characterized by a selection step which is performed in conditions of pH suitable to create "positive patches" on the surface of the protein target. In other words, the process conceived by the Applicant is based on the enhancement of the local interactions between the potential aptamers and the targeted protein by promoting positive charges on a surface domain of the protein. The Applicant calls this method "locally enhanced electrostatic interaction SELEX".

This method can be implemented in particular for proteins having one or several surface histidines, in particular a histidine-containing surface domain and known or expected to have unfavourable properties for interactions with polyanions such as nucleic acids.

Noteworthy, the method of the invention does not require the use of sophisticated chemically-modified oligonucleotides libraries and can be implemented from any oligonucleotide libraries. The method of the invention also enables to obtain aptamers displaying binding properties suitable for use as affinity ligands in purification process. Indeed, the method of the invention provides aptamers which specifically bind to their target, and allows mild elution conditions in chromatography process. In particular, an aptamer obtained by the method of the invention and its targeted protein may interact in a pH-dependent manner, whereby the release of the targeted protein from the complex formed between the aptamer and the said protein may be obtained in mild and gently conditions by adjusting the pH conditions.

The Applicants validated the method of the invention for two protein models, namely fibrinogen and the Fc fragment of immunoglobulin of the G isotype (IgG).

Certainly, aptamers which potentially bind to fibrinogen have been described in the prior art. PCT application, WO2010/019847 describes aptamers directed against fibrinogen and fibrin and comprising at least one nucleotide having a boronic moiety (i.e. a boronic acid-modified nucleotide). US patent application 2013-0245243 in the name of Base Pair Technologies describes several potential anti-fibrinogen aptamers, but does not provide any evidence showing the actual affinity and specificity of these aptamers for fibrinogen. EP 1 918 372 in the name of Ribomic describes several RNA aptamers against IgGs.

Base Pair Biotechnologies also markets aptamers stated as anti-fibrinogen (reference 6F01 oligo #370) or anti-IgG (reference CO2 oligo #369) aptamers for research use only.

The Applicants investigated the ability of said aptamers to be used as affinity ligands for the purification of fibrinogen and IgGs. The experiments performed by the Applicant demonstrated that said aptamers did not have binding properties suitable for use as affinity ligands. As shown in FIG. 11A, the anti-fibrinogen aptamer marketed by Base Pair Biotechnologies (reference 6F01 oligo #370) displayed very low binding to both transgenic and human fibrinogen, even with the binding buffer recommended by the manufacturer. This low binding capacity precludes its use as affinity ligand in purification process. Similarly, the Applicant showed that aptamer ATW0018 marked by Base Pair technologies had a low binding to plasma polyclonal IgG (see FIG. 11B)

Then, the Applicants carried-out several SELEX strategies described in the prior art to identify aptamers against human fibrinogen or human IgG. None of these strategies succeeded. Noteworthy, SELEX process implemented for obtaining anti-fibrinogen aptamers led to the identification of aptamers directed against a contaminant accounting for less than 1% in the purified fibrinogen composition used for implementing SELEX process. On the other hand, standard SELEX, performed to identify aptamers directed against the Fc fragment derived from a monoclonal IgG, also failed and led to the identification of aptamers against the hypervariable region of the monoclonal IgG, which was present in trace amounts in the Fc preparation.

Noteworthy, all the SELEX strategies described in the prior art and tested by the Applicant encompass selection steps performed at physiological pH, around pH 7.5

As fully-described in the below examples, by implementing the selection step of SELEX process at a pH value promoting the formation of "positive patches" on the protein target surface, for instance at pH 6.3 for fibrinogen and at pH 5.5 for IgG, the Applicant obtained several aptamers displaying appropriate binding properties for IgG and fibrinogen, respectively, and which can be used as affinity ligands in the purification of said proteins, even from complex medium such as plasma, at the industrial scale. Noteworthy, the aptamers obtained by the process of the invention may bind to their protein target in pH-dependent manner. Such property is particularly suitable for use in affinity chromatography because the formation of the complex between the protein target to purify and the aptamer, and the subsequent release of the protein target from the complex can be controlled by merely modifying the pH of the elution buffer. In other words, the elution can be performed in mild and selective conditions which are not likely to denature the protein target.

·Method for Obtaining an Aptamer Against a Protein Target Comprising a Histidine-Containing Surface Domain In a first aspect, the invention relates to a method for obtaining an aptamer against a protein target comprising a histidine-containing surface domain, said method comprising:
  a) contacting the protein target with a candidate mixture of nucleic acids at a pH promoting the formation of at least one positive charge on said histidine-containing surface domain of the protein target, and in conditions favourable for the binding of the protein target with nucleic acids having affinity for said target,
  b) recovering nucleic acids which bind to the protein target, while removing unbound nucleic acids,
  c) amplifying the nucleic acids obtained in step (b) to yield to a candidate mixture of nucleic acids with increased affinity to the protein target, and
  d) repeating steps (a), (b), (c) until obtaining one or several aptamers against the protein target.

As used herein, an "aptamer" (also called herein "nucleic aptamer" or "nucleic ligand") refers to a synthetic single-stranded oligonucleotide typically comprising from 20 to 150 nucleotides in length and able to bind with high affinity to a target molecule. The aptamers are characterized by three-dimensional conformation(s) which may play a key role in their interactions with their target molecule. The interactions between an aptamer and its target molecule may include electrostatic interactions, hydrogen bonds, aromatic stacking and shape complementarity. The aptamer displays a high affinity for its target molecule. The dissociation constant (Kd) of an aptamer for its target molecule is typically from $10^{-6}$ to $10^{-12}$ M, preferably from $10^{-8}$ to $10^{-12}$ M. Typically, the aptamer specifically binds to its target molecule. The term "specifically binding" is used herein to indicate that the aptamer has the capacity to recognize and interact specifically with its target molecule, while having relatively little detectable reactivity with other molecules which may be present in a sample. Preferably, the aptamer specifically binds to its target molecule if its affinity is significantly higher for the target molecule, as compared to other molecules, including molecules structurally close to the target molecule.

For instance, an aptamer might be able to specifically bind to a human protein while displaying a lower affinity for a homolog of said human protein.

As used herein, "an aptamer display a higher affinity for its target molecule as compared to a given molecule" or "an aptamer is specific to its target molecule as compared to a given molecule" means that the dissociation constant (Kd) of the aptamer for its target molecule is at least 5-fold, preferably, at least 10, 20, 30, 40, 50, 100, 200, 500, or 1000-fold lower than the Kd of said aptamer for the given molecule. In some embodiments, the aptamer does not bind to the given molecule, which means that the possible association of the aptamer with said given molecule is undetectable. Kd is preferably determined by surface plasmon resonance.

The aptamer may be a deoxyribonucleic acid (DNA) or a ribonucleic acid (RNA). The aptamer may comprise one or several chemically-modified nucleotides as detailed further below.

As used herein, "a protein target" is virtually any protein for which aptamers are sought. In the context of the above-detailed process, said protein target comprises at least one surface histidine and in particular a histidine-containing surface domain.

As used herein, "Surface amino acids" refer to amino acid residues which are on the surface of the protein, namely exposed to the bulk solvent.

Accordingly, "a surface histidine" refers to a histidine residue of the protein target which is exposed to the environment and thus accessible to the solvent. In some embodiments, said protein target may comprise at least 2, 3, 4, 5, 6, 7, 8, 9, or 10 surface histidines.

The protein target comprises a histidine-containing surface domain, whereby in step a), the pH is selected so as to promote the formation of positive charges on said histidine-containing surface domain. Preferably, the pH is selected so as to protonate the at least one surface histidine(s) present in the histidine-surface containing domain.

As used herein, "A histidine-containing surface domain" refers to a surface domain comprising at least one surface histidine residue, i.e. one histidine surface residue or several surface histidine residues. The wording "several surface histidine residues" encompasses at least 2, 3, 4, 5, 6, 7, 8, 9, or 10 histidine residues.

In some embodiments, the histidine-containing surface domain contains one single surface histidine. Indeed, one surface histidine may be sufficient to promote interaction with aptamers.

In other embodiments, the "histidine-containing surface domain" may contain several histidine residues, such as 2, 3, 4 or 5. In some embodiments, such histidine residues may be close to each other, for instance at a distance of about 10-20 Angstrom.

A histidine-containing surface domain is typically a surface domain of the protein target containing (i) the at least one surface histidine residue and (ii) the surface amino acid residues which are in the vicinity of the at least surface histidine. The vicinal amino acid residues may be for instance at a distance of less than 60 (e.g. less than 50, 40 or 30) Angstrom of said at least one surface histidine residue.

The histidine-containing surface domain may account for 0.5% to 60%, preferably from 0.5% to 10% of the total surface area of the target protein.

In some embodiments, the target protein may comprise several histidine-containing surface domains, for instance at least 2, 3, 4, 5, 6, 7, 8, 9 or 10 histidine-containing surface domains. When the target protein comprises several histidine-containing surface domains, it may be sufficient to create a positive charge on one histidine-containing surface domain to promote interactions with aptamers. For a given protein, the presence of "surface histidine residue(s)" and "histidine-containing surface domain" can be determined by molecular modelling from the primary sequence of the protein. For instance, the tertiary or quaternary structure of the protein can be predicted from the primary amino acid sequence by using modelling software such as Modeller software (www.salilab.org/modeller/) by comparison with homologous proteins.

Alternatively, the presence of "a histidine-containing surface domain" can also be determined from the crystalline structure of the protein. Methods for obtaining protein crystals are well-known by the skilled artisan.

In some embodiments, the histidine-containing surface domain has a positive electrostatic surface potential at a pH lower than 7.0, preferably lower than 6.5, for instance lower than 6.0. In a preferred embodiment, histidine-containing surface domain is not a HIS tag domain, e.g. a polyhistidine moiety introduced on the N-extremity or C-extremity of the protein for purification purpose.

In particular, the protein of interest may be any "SELEX-resistant" protein, i.e. any protein for which basic SELEX, i.e. SELEX process performed on an unmodified oligonucleotide library as described in WO9119813 fails.

In some embodiments, the protein target of interest may be any protein which displays unfavourable properties for interactions with polyanions, in particular with nucleic acids, at physiological pH, namely at a pH around 7.0.

Such proteins encompass, without being limited to:
proteins having an isoelectric point (pI) of less than 7.5, preferably less than 7.0,
proteins which are devoid of any surface domain with a positive surface electrostatic potential at a pH of more than 7.0.

Generally, the pI of a given protein does not refer to a single value but is rather defined as a value range. For instance, the pI of fibrinogen is from 5.10 to 6.3. As used herein, a protein having a pI of less than 7.5 means that the upper value of the pI range is lower than 7.5.

A protein having an isoelectric point of less than 7.5, encompasses a protein having a pI of less than 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, or 5.5. For instance, the, pI of the protein may be from 4.0 to 6.9.

In some embodiments, the protein of interest used in the SELEX process of the invention is devoid of any HIS tag In some embodiments, the protein target of interest has the amino acid sequence of a human wild-type protein or is a variant or a fragment of a human wild-type protein.

As used herein, a variant of a wild-type protein refers to a protein having at least 80% of sequence identity, preferably at least 85%, 90%, or 95% of sequence identity with said wild-type protein and which displays a similar biological activity as compared to said wild-type fibrinogen. The variant may have an increased or a decreased biological activity as compared to the corresponding wild-type protein. In some embodiments, the protein target is a recombinant protein, for instance obtained from a recombinant host cell, or a recombinant pluricellular organism, such as a transgenic animal.

In some alternate or additional embodiments, the protein target is selected from the group consisting of fibrinogen, immunoglobulins and fragments or variants thereof as well as proteins containing a Fc region.

As used herein, "Fc", "Fc Fragment" or "Fc region" refers to the polypeptide comprising the constant region of an antibody excluding the first constant region immunoglobulin domain. Thus, Fc refers to the last two constant region immunoglobulin domains of IgA, IgD, and IgG, the last three constant region immunoglobulin domains of IgE and IgM, and the flexible hinge N-terminal to these domains.

By "immunoglobulin" or "full-length antibodies" as used herein is meant the structure that constitutes the natural biological form of an antibody, including variable and constant regions. "Full length antibody" covers monoclonal full-length antibodies, wild-type full-length antibodies, chimeric full-length antibodies, humanized full-length antibodies, the list not being limitative. In most mammals, including humans and mice, the structure of full-length antibodies is generally a tetramer. Said tetramer is composed of two identical pairs of polypeptide chains, each pair having one "light" (typically having a molecular weight of about 25 kDa) and one "heavy" chain (typically having a molecular weight of about 50-70 kDa). In some mammals, for example in camels and lamas, full-length antibodies may consist of only two heavy chains, each heavy chain comprising a variable domain attached to the Fc region. Such antibodies are called heavy chain antibodies. Heavy chain antibodies also encompass IgNar from cartilaginous fishes.

In some embodiments, the protein target is a protein containing a human Fc fragment, in particular an immunoglobulin, a Fc-fusion protein or a Fc-conjugate.

In the case of human immunoglobulins, light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

In some embodiments, the protein target may contain a Fc fragment from a human immunoglobulin, in particular from a IgG.

The immunoglobulin (Ig) may be a naturally-occurring Ig, a variant of a naturally-occurring Ig, a recombinant Ig, a chimeric Ig, a humanized Ig.

For instance, the target protein may be selected from the group consisting of plasma human fibrinogen, recombinant human fibrinogen, variants of human fibrinogen, fragments of human fibrinogen, plasma human IgG, recombinant human IgG, chimeric IgG, humanized IgG, variants of human IgG, Fc fragment from human IgG and Fc variants from human IgG.

Step (a) comprises contacting the protein target with a candidate mixture of nucleic acids at a pH promoting the formation of positive charges on the histidine-containing surface domain of said protein target.

The candidate mixture of nucleic acids is generally a mixture of chemically synthesized random nucleic acid. The candidate mixture may comprise from $10^8$ to $10^{18}$, typically about $10^{15}$ nucleic acids. The candidate mixture may be a mixture of DNA nucleic acids or a mixture of RNA nucleic acids. In some embodiments, the candidate mixture consists of a multitude of single-stranded DNAs (ssDNA), wherein each ssDNA comprises a central random sequence of about 20 to 100 nucleotides flanked by specific sequences of about 15 to 40 nucleotides which function as primers for PCR amplification. In some other embodiments, the candidate mixture consists of a multitude of RNA nucleic acids, wherein each RNA comprises a central random sequence of about 20 to 100 nucleotides flanked by primer sequences of about 15 to 40 nucleotides for RT-PCR amplification. In some embodiments, the candidate mixture of nucleic acids consists of unmodified nucleic acids, this means that the nucleic acids comprise naturally-occurring nucleotides only. In some other embodiments, the candidate mixture may comprise chemically-modified nucleic acids. In other words, the nucleic acids may comprise one or several chemically-modified nucleotides. The chemical modification(s) can be performed in order to improve the stability of the nucleic acids, for instance to nucleases. In RNAs, the ribose 2'-OH group of pyrimidine may be replaced with a 2'-NH2, 2'-F, or a 2'-OMe. Chemical modifications can be also introduced on the C-5 position of pyrimidines or at C-8 position of purines. Alternatively, modifications in the phosphate backbone of nucleic acids can be introduced by replacing a phosphodiester linkage by phosphorothioate linkage. Other modifications can be introduced for quantification purpose during the SELEX process such as the incorporation of radioactive labelled nucleotides or the attachment of fluorescent molecule to the 5'-end of the nucleic acids.

In some embodiments, the candidate mixture of nucleic acids is devoid of any 5-modified deoxyuridine-containing nucleic acids. In some other embodiments, the candidate mixture is devoid of any 5-modified pyrimidine-containing nucleic acids and/or any boronic acid-modified nucleotides. In some further or additional embodiments, the candidate mixture of nucleic acids is devoid of any nucleic acids comprising chemically-modified nucleotides. In other words, the candidate mixture of nucleic acids consists of nucleic acids comprising naturally-occurring nucleotides only. In some other embodiments, the candidate mixture comprises nucleic acids having a chemically-modified nucleotide at their 5'-end and/or 3'-end only. In preferred embodiments, the candidate mixture consists of single-stranded DNAs.

In step (a), the target protein and the candidate mixture are contacted in pH conditions enabling positive charges to be formed on at least one of the histidine-containing surface domains of the target protein. In particular, the pH of step (a) may be selected so as to promote the protonation of the histidine residue(s) present in a histidine-containing surface domain.

Indeed, the pKa of histidine in free-state is 6.0. However, the pKa of the histidine in protein structure may vary depending on the amino acids present in its vicinity. The pH of step (a) is generally below than 7.0 and preferably around pH 6.0.

The pH to implement step (a) depends on the protein target of interest, but is typically selected from pH 4.0 to 6.9, preferably from 5.0 to 6.9 such as a pH of 5.3 to pH 6.7. A pH of 5.3 to pH 6.7 encompasses a pH of 5.3 to 5.5, a pH of 5.5 to 5.7, a pH of 5.7 to 5.9, a pH of 5.9 to 6.1, a pH of 6.1 to 6.3, a pH of 6.3 to 6.5, and a pH of 6.5 to 6.7. For instance, if the protein target is human fibrinogen, step (a) may be performed at a pH of 6.2 to 6.6, for instance of about 6.3.

As another example, if the target protein is a human immunoglobulin of G isotype or human Fc fragment thereof, step (a) may be performed at a pH of 5.0 to 6.0, for instance 5.5.

Typically, the pH of step (a) may be selected so that the electrostatic surface potential of the histidine-containing surface domain is positive.

The skilled artisan may determine the appropriate pH to use in step (a) by molecular modelling, in particular by determining the surface charge distribution. Typically, the pH of step (a) can be determined by generating the surface electrostatic potential maps of the protein at different pHs. The surface electrostatic potential maps of the protein target may be obtained by a software which calculates the electrostatic surface potential from crystal structures or homology models. For instance, one may use PDB2PQR software (Dolinsky et al. Nucleic Acids Research 32 W665-W667 (2004) or Pymol software equipped with APBS plugin (Baker et al., Proc. Natl. Acad. Sci. USA 98, 10037-10041 2001).

Accordingly, in some embodiments of the invention, the pH used in step a) is identified by surface electrostatic potential mapping at different pHs.

It goes without saying that the pH for step (a) is also selected in view of the pH stability of the target protein. Typically, the pH of step (a) is selected in the pH range wherein the protein target is stable. Thus, the pH of step (a) may be selected so as to promote a positive electrostatic surface potential on the histidine-containing surface domain while being in the pH stability range for the target protein. For instance, the pH of step (a) may be selected so as to be included in the pH stability range of the target protein and sufficiently distant from the upper and the lower limits of the range, typically by a $\Delta pH$ of at least 0.1, such as a $\Delta pH$ of at least 0.2, 0.3, 0.4 or 0.5.

In other words, the pH of step (a) may be determined as a pH value included in the pH stability range of the protein target and which enables to promote a positive electrostatic surface potential on at least one histidine-containing surface domain of said protein target.

In step (a), the target protein and the candidate mixture are contacted at the desired pH and in conditions enabling the formation of complex between the protein target and nucleic acids displaying affinity for said protein target. Such conditions favourable for the binding of the protein target to nucleic acids having affinity to said targets comprise appropriate conditions of temperature, ionic strength and period of incubation. The candidate mixture is incubated with the protein target for a period of time sufficient to enabling the formation of the complexes. Typically, the incubation may last several minutes to several hours, for instance from 10 minutes to 2 hours. A complex corresponds to the binding of a nucleic acid to a molecule target, i.e. to nucleic acid-protein target pair.

Step (a) may be performed in a buffered aqueous solution. The buffering agent may be selected from any buffer agents enabling to obtain the desired pH and compatible with the protein targets and the nucleic acids mixture.

The buffer agent may be selected from, without being limited to, 3-(N-morpholino)propanesulfonic acid (MOPS), 2-(N-morpholino)ethanesulfonic acid (MES), HEPES, Bis-TRIS, citrate and acetate. The buffering agent may be present at a concentration of about 5 mM to 1 M, for instance from 10 mM to 500 mM, for instance from 10 mM to 200 mM such as about 50 mM.

In some embodiments, the protein target may be present in free-state in step (a). In some other embodiments, the protein target may be immobilized on a solid support in order to make easier the subsequent separation of the complex formed by the protein target with certain nucleic acids and the unbound nucleic acids in step (b). For instance, the protein target may be immobilized onto magnetic beads, on solid support for chromatography such as sepharose or agarose, on microplate wells and the like. Alternatively, the protein target may be tagged with molecules useful for capturing of the complex in step (b). For instance, the protein target may be biotinylated.

Step (b) aims at recovering nucleic acids which bind to the protein target in step (a), while removing unbound nucleic acids. Typically, step (b) comprises separating the complex formed in step (a) from unbound nucleic acids, and then releasing the nucleic acids from the complex whereby a new mixture of nucleic acids with increased affinity to the target protein is obtained. The separation of the complex from the unbound nucleic acids may be performed by various methods and may depend on the features of the protein target. These methods include without being limited to, affinity chromatography, capillary electrophoresis, flow cytometry, electrophoretic mobility shift, Surface Plasmon resonance (SPR), centrifugation, ultrafiltration and the like. The skilled artisan may refer to any separation methods described in the state in the art for SELEX processes, and for instance described in Stoltenburg et al. Biomolecular Engineering, 2007, 24, 381-403, the disclosure of which being incorporating herein by reference. As illustration only, if the protein target is immobilized on a support, the separation may be performed by recovering the support, washing the support with an appropriate solution and then releasing nucleic acids from the complex immobilized on the support. If the protein target has been incubated in free-state with the candidate mixture, the separation of the nucleic acid-protein complex from unbound nucleic acids can be performed by chromatography by using a stationary support able to specifically bind to the protein target or the possible tag introduced on the protein target, whereby the complexes are retained on the support and the unbound nucleic acids flow out. For instance, one may use a stationary phase having thereon antibodies directed against the target protein. Alternatively, the partitioning may be performed by ultrafiltration on nitrocellulose filters with appropriate molecular weight cut-offs. Once the complexes separated from unbound nucleic acids, the nucleic acids which bind to the protein target are released from the complexes. The release can be performed by denaturing treatments such as heat treatment or by elution.

The dissociation between the protein target and the bound nucleic acids may be performed by increasing the ionic strength or by modulating the pH in the buffer used in step b) as compared to the buffered solution used in step a).

Preferably, the dissociation is obtained by increasing the pH in step b) as compared to step a). In the present case, the pH used in step b) may be higher than the pH used in step (a) of a ΔpH of at least 0.3, preferably of at least 0.5, 0.6, 0.7, 0.8, 0.9, 1.0, 1.1, 1.2, 1.3, 1.4, or 1.5. In particular, the pH may be included in the pH range defined by [$pH_{step(a)}$+0.5; $pH_{step(a)}$+1.5]. For instance, if the pH of step (a) is 6.4, the pH of the elution buffer may be from 6.9 to 7.9, such as 7.4.

Typically, in step b) a pH of more than 7.0, in particular a pH from 7.0 to 8.0 such as 7.1, 7.2, 7.3, 7.4, 7.5, 7.6, 7.7, 7.8, 7.9, or 8.0 may be used to dissociate the complex and thus recover the nucleic acids binding to the protein target.

In alternate or additional embodiments, the elution buffer may comprise EDTA or detergent such as SDS, or urea. For instance, the elution buffer may comprise EDTA at a concentration of about 100 mM to 500 mM. In some other embodiments, the elution buffer is devoid of EDTA and/or any detergent.

In a preferred embodiment, in step b), the step of releasing the nucleic acids from the complex comprises a step of dissociating the complex by increasing the pH at a value higher than that used in step a) of a ΔpH of at least 0.8 such as 1.0. Typically, the elution buffer in step b) may have a pH above 7.0, preferably from 7.0-8.0 e.g. 7.2 to 7.8, for instance 7.3, 7.4, 7.5, 7.6 or 7.7. Preferably, the complex is immobilized on a solid support by the mean of the protein target. This means that the protein target is immobilized by covalent or non-covalent interactions on the solid support as described above. After an optional washing step, typically with the buffer used in step a), the complex between the bound nucleic acids and the protein target can be dissociated with an elution buffer having a pH of at least 7.0, typically from 7.0 to 8.0. The nucleic acids are thus recovered in the elution buffer. In some embodiments, such step is performed by chromatography.

Without to be bound by any theory, the Applicant believes that using such mild conditions of dissociation in step b) may enable to select aptamers with appropriate binding properties for use in purification. In particular, the switch of pH between step (a) and step (b) can add selectivity, whereby aptamers binding to the protein target in a pH-dependent manner can be identified.

In step (c), the nucleic acids recovered in step (b) are amplified so as to generate a new mixture of nucleic acids. This new mixture is characterized by an increased affinity to the target protein as compared to the starting candidate mixture.

The amplification may be performed by any method enabling to increase the amount or the number of nucleic acid copies. For RNAs, the amplification is typically performed by reverse transcription PCR (RT-PCR). In the case of DNAs, the amplification is performed by PCR (Polymerase Chain Reaction), which leads to double-stranded DNAs. The double-stranded DNAs are then separated into single-stranded DNAs so as to obtain a new mixture of single-stranded DNAs. The separation of the "wanted" strands from their "complementary unwanted strands" can be performed by various methods described in the state in the art.

For instance, one can use the streptavidin/biotin system. A biotin molecule can be added onto the unwanted strand during the amplification. The double-stranded DNAs may be then immobilized on streptavidin-coated surface and the wanted single-stranded DNAs can be recovered after DNA denaturation while the unwanted strands remain immobilized onto the surface. Other possibilities is to perform asymmetric PCR in which specific primers are used to create a size difference between the "wanted strands" and the "unwanted strands" whereby they can be separated for instance by subsequent electrophoresis.

Step (a), (b) and (c) form together a round of selection. As indicated in step (d), this round of selection can be repeated several times, typically 6-20 times until obtaining an aptamer or a pool of aptamers directed against the target protein. It goes without saying that the step (a) of round "N" is performed with the mixture of nucleic acids obtained in step (c) of the round "N−1". At the end of each selection round, the complexity of the mixture obtained in step (c) is reduced and the enrichment in nucleic acids which specifically bind to the target protein is increased.

The conditions for implementing step (a), (b) and (c) may be the same or may be different from one round of selection to another. In particular, the conditions of step (a) (e.g. the incubation conditions of the target protein with the mixture of nucleic acids) can change. For instance, step (a) of round "N" can be performed in more drastic conditions than in round "N+1" in order to direct the selection to aptamers having the highest affinity for the protein target. Typically, such result can be obtained by increasing the ionic strength of the buffer used in step (a).

The method of the invention may comprise one or several additional steps.

In particular, the process may comprise a step, prior to step (a), of determining the pH for implementing step (a).

The pH to be used in step (a) may be determined by molecular modelling as described above.

In some embodiments, such step comprises modelling the surface electrostatic maps of the protein at different pHs and selecting a pH for implementing step a) which enables to create a positive surface electrostatic potential on the histidine-containing surface domain and which belongs to the pH stability range of the protein.

The method of the invention may comprise counter-selection or subtractive selection rounds. The counter-selection rounds may aim at eliminating nucleic acids which cross-react with other entities or directing the selection to aptamers binding to a specific domain of the protein target. The additional counter-selection round(s) depend on the contemplated use of the final aptamers. If the aptamer is to be used as affinity ligand for the purification of a transgenic human protein expressed in a transgenic animal naturally expressing a protein homologous to said human protein, the method of the invention may comprise a step of removing aptamers which binds to said homologous protein. Thus, the method may comprise one or several rounds of selection wherein aptamers binding to a protein homologous to the protein target are removed.

Alternatively, the method of the invention may comprise additional round(s) of selection in order to identify aptamers able to bind to the target protein regardless its glycosylation state.

For illustration, the first selection rounds can be performed with a non-recombinant protein target, and the subsequent selection rounds can be performed with a recombinant protein target produced in transgenic animal or in host cell such as bacterium or yeast. As an example, in order to identify aptamers capable of specifically binding to human fibrinogen from human plasma and to human fibrinogen produced in transgenic animal, certain rounds of selection may be performed with human plasma fibrinogen as protein target and the remaining rounds of selection may be performed with transgenic human fibrinogen as protein target.

The method of the invention may also comprise one or several additional steps following the generation of the final pool of aptamers.

The method of the invention may comprise one or several of the following steps:
- a step of cloning the aptamer pool,
- a step of sequencing an aptamer,
- a step of producing an aptamer, for instance by chemical synthesis,
- a step of identifying consensus sequences in the pool of aptamers, for instance by sequence alignment,
- a step of optimizing the sequence of an aptamer, In some embodiments, the method of the invention may comprise the following additional steps:
- sequencing an aptamer obtained in step (c)
- optimizing said aptamer, and
- producing the optimized aptamer, preferably by chemical synthesis.

The optimization of the aptamer may comprise the determination of the core sequence of the aptamer, i.e. the determination of the minimal nucleotide moiety able to specifically bind to the protein target. Typically, truncated versions of the aptamer are prepared so as to determine the regions which are not important in the direct interaction with the protein target.

The binding capacity of the starting aptamer and the truncated versions may be assessed by any appropriate methods such as SPR.

Alternatively or additionally, the sequence of the aptamer may be subjected to mutagenesis in order to obtain aptamer mutants, for instance with improved affinity or specificity as compared to their parent aptamer. Typically one or several nucleotide modifications are introduced in the sequence of the aptamer. Nucleotide modifications include the deletion of a nucleotide, the insertion of a nucleotide or the replacement of a nucleotide by another nucleotide. The resulting mutants are then tested for their ability to specifically bind to the protein target, for example by SPR or ELISA-type assay.

In additional or alternate embodiments, the optimization may comprise introducing one or several chemical modifications in the aptamer. Typically, such modifications encompass replacing nucleotide(s) of the aptamer by corresponding chemically-modified nucleotides. The modifications may be performed in order to increase the stability of the aptamers or to introduce chemical moiety enabling functionalization or immobilization on a support. Appropriate chemical modifications are those detailed above and encompass 2'-ribose modifications such 2'-F, 2'-NH2, and 2'-OMe, phosphorothiate replacement of phosphodiester group and the likes. Caps such as amine, phosphate, PEG, cholesterol fatty acids and the like may be introduced at the 3' and/or 5'-end of the aptamer. At last, the chemical modifications may encompass the introduction of labels or tags such as biotin, fluorescent molecules, dyes, and the like at the 3' and/or 5' end of the aptamer.

Particular Embodiments of the Method of the Invention

In a particular aspect, the invention relates to a method for obtaining an aptamer against fibrinogen, said method comprising:
- a) contacting fibrinogen with a candidate mixture of nucleic acids at a pH lower than 7.0, preferably from 5.8 to 6.8,
- b) recovering nucleic acids which bind to fibrinogen, while removing unbound nucleic acids,
- c) amplifying the nucleic acids obtained in step (b) to yield to a candidate mixture of nucleic acids with increased affinity to fibrinogen, and
- d) repeating steps (a), (b), (c) until obtaining one or several aptamers against fibrinogen.

Step a) is performed in conditions favourable for the binding of fibrinogen with nucleic acids having affinity for said fibrinogen. Preferably, the pH of step a) is from 6.0 to 6.6, such as 6.1, 6.2, 6.3, 6.4 and 6.5.

An appropriate pH for step a) is for instance, 6.3±0.1. Such pH enables to protonate at least one surface histidine of fibrinogen.

Preferably, fibrinogen is a human fibrinogen or a variant thereof. Fibrinogen may be a plasma human fibrinogen or a transgenic human fibrinogen, as explained in section entitled "Method for obtaining an aptamer against a protein target comprising a histidine-containing surface domain".

Step b) typically comprises the steps of separating the complex formed in step (a) from unbound nucleic acids, and then releasing the bound nucleic acids from the complex. The dissociation of the complex between fibrinogen and bound nucleic acids can be performed by increasing the pH above 7.0 in step b). Typically, in step b) the nucleic acids are recovered by dissociating the complex between fibrinogen and the nucleic acids at a pH above 7.0, for instance from pH 7.0 to 8.0, preferably from pH 7.2 to 7.8, more preferably from 7.2 to 7.6, such as 7.4.

In preferred embodiments, in step b), the complex is immobilized on a solid support by the mean of the protein target. This means that the protein target is immobilized by covalent or non-covalent interactions on the solid support as described above. After an optional washing step, typically with the buffer used in step a), the complex between the nucleic acids and the protein target can be dissociated with an elution buffer having a pH from pH 7.0 to 8.0, preferably from pH 7.2 to 7.8, more preferably from 7.2 to 7.6, such as 7.4. The nucleic acids are thus recovered in the elution buffer.

In another particular aspect, the invention relates to a method for obtaining an aptamer against a target protein selected from a Fc-containing protein, or a Fc fragment, said method comprising:
- a) contacting the target protein with a candidate mixture of nucleic acids at a pH lower than 7.0, preferably from 5.0 to 6.0,
- b) recovering nucleic acids which bind to the protein target, while removing unbound nucleic acids,
- c) amplifying the nucleic acids obtained in step (b) to yield to a candidate mixture of nucleic acids with increased affinity to the protein target, and
- d) repeating steps (a), (b), (c) until obtaining one or several aptamers against the protein target.

Step a) is performed in conditions favourable for the binding of the target protein with nucleic acids having affinity for said fibrinogen.

Preferably, the pH of step a) is from 5.2 to 5.8, such as 5.3, 5.4, 5.5, 5.6, and 5.7. An appropriate pH for step a) is for instance 5.5±0.1.

Preferred Fc-containing proteins are immunoglobulins as defined in the above section, preferably human immunoglobulins from human plasma or recombinantly produced.

Step b) typically comprises the steps of separating the complex formed in step (a) from unbound nucleic acids, and then releasing the nucleic acids from the complex. The dissociation of the complex between the protein target and the bound nucleic acids can be performed by increasing the pH above 6.0 in step b). Typically, in step b) the nucleic acids are recovered by dissociating the complex at a pH above 7.0, for instance from pH 7.0 to 8.0, preferably from pH 7.2 to 7.8, more preferably from 7.2 to 7.6, such as 7.4.

In preferred embodiments, in step b), the complex is immobilized on a solid support by the mean of the protein target. This means that the protein target is immobilized by covalent or non-covalent interactions on the solid support as described above. After an optional washing step, typically with the buffer used in step a), the complex between the nucleic acids and the protein target can be dissociated with an elution buffer having a pH from pH 7.0 to 8.0, preferably from pH 7.2 to 7.8, more preferably from 7.2 to 7.6, such as 7.4. The nucleic acids are thus recovered in the elution buffer.

It goes without saying that the conditions to implement steps a), b), c) and d) in the two above methods may be as defined in the section entitled "Method for obtaining an aptamer against a protein target comprising a histidine-containing surface domain".

Method for Obtaining an Aptamer Against any Protein Target

In another aspect, the invention relates to a method for obtaining an aptamer against a protein target, which comprises:
(i) determining a pH value promoting positive charges in at least one surface domain of the protein target,
  a. contacting the protein target with a candidate mixture of nucleic acids at the pH determined in step (i) in conditions favourable for binding of the protein target with nucleic acids having affinity for said targets,
  b. recovering nucleic acids which bind to the protein target, while removing unbound nucleic acids,
  c. amplifying the nucleic acids obtained in step (b) to yield to a candidate mixture of nucleic acids with increased affinity to the protein target,
  d. repeating steps (a), (b), (c) until obtaining one or several aptamers against the protein target of interest.

The conditions to implement steps a), b), c) and d) may be as defined above in the section entitled "Method for obtaining an aptamer against a protein target comprising a histidine-containing surface domain" except for the condition of pH in step (a) which is determined as stated in step (i).

The protein target may be any protein target of interest. In particular, the protein target may be selected among the group consisting of antibody, antigen, growth factor, receptor, enzyme, glycoprotein, a fragment or variant thereof. In certain embodiments, the protein target is a plasma protein such as immunoglobulin and fibrinogen.

Step (i) can be typically performed by molecular modelling by using software such as Modeller. In some embodiments, the molecular modelling may be based on data obtained from crystalline structure of the protein. In other embodiments, the molecular modelling may be performed from the primary sequence of the protein by comparison with homologous proteins for which the three-dimensional structure is known.

Preferably, the pH determined in step (i) enables to create a positive surface electrostatic potential in at least one surface domain of the protein target. Typically, step (i) may comprise the modelling of the electrostatic potential maps for the protein target at different pHs by using modelling software such as Modeller. The pH of interest is selected among the pH(s) enabling to generate a positive surface electrostatic potential on at least one surface domain of the protein, in view of the pH stability range of the protein. In other words, the pH in step (i) is selected in the overlap of the pH stability range of the target protein and the pH range enabling the presence of a positive surface electrostatic potential on a surface domain of the protein target.

In some embodiments, step (i) may comprise the steps of:
 determining the presence of a histidine-containing surface domain in the protein target, and
 if said domain is present, determining a pH promoting positive charges, preferably enabling to obtain a local positive electrostatic potential, in said histidine-containing surface domain.

As mentioned above, for a given protein, the presence of "a histidine-containing surface domain" can be determined by molecular modelling from the primary sequence of the protein. For instance, the tertiary or quaternary structure of the protein can be predicted from the primary amino acid sequence by using modelling software such as Modeller by comparison with homologous proteins. The presence of "a histidine-containing surface domain" can also be determined from the crystalline structure of the protein.

It goes without saying that said method may comprise one or several additional steps such as those listed for the "Method for obtaining an aptamer against a protein target comprising a histidine-containing surface domain". In particular, said method may comprise one or several of the following steps:
 a step of counter-selection
 a step of cloning the aptamer pool,
 a step of sequencing an aptamer,
 a step of producing an aptamer, for instance by chemical synthesis,
 a step of identifying consensus sequences in the pool of aptamers, for instance by sequence alignment, and
 a step of optimizing the sequence of an aptamer, Aptamers of the Invention and Uses Thereof Without to be bound by any theory, the Applicant is of the opinion that the methods of the invention enable to obtain aptamers which differ from the aptamers described in the prior art in virtue of their unique binding properties. In particular, said aptamers specifically bind to the protein of interest as defined above with a high affinity. The dissociation constant (Kd) of said aptamer for their target molecule is typically from $10^{-12}$ to $10^{-6}$ M, preferably from $10^{-12}$ to $10^{-8}$ M. Noteworthy, the aptamers obtained by the method of the invention may bind to their protein target in a pH-dependent manner. As illustrated in the example, the anti-fibrinogen aptamers identified by the method of the invention specifically bind to fibrinogen at pH 6.3, and not at pH 7.4. Similarly, the identified anti-Fc aptamers specifically bind to IgG at pH 5.5 and not at pH 7.4.

As used herein, an aptamer binds to its protein target in a pH-dependent manner means that the affinity of the aptamer for its protein target depends on the pH. In particular, the dissociation constant (Kd) may vary depending on the pH. In the context of the invention, the aptamer may have a higher affinity at a slightly acid pH as compared to physiological pH. In other words the Kd of the aptamer may be at least 2-fold higher, in particular, at least 5, 10, 20, 50, 100, 500, or 1000-fold at physiological pH than at slightly acid pH. Typically a physiological pH is a pH of about 7.0-7.8, preferably from 7.0 to 7.7 such as 7.0-7.5, in particular 7.2, 7.3 or 7.4.

A slightly acid pH is typically a pH from 4.5 to 6.9, such as 5.0 to 6.8. For instance, a slightly acid pH may be from 5.3 to 5.7, e.g. 5.5, if the protein target is an immunoglobulin or a Fc fragment. A slightly acid pH may be from 6.0 to 6.5, e.g. 6.3 or 6.4, if the protein target is a fibrinogen.

In some preferred embodiments, the aptamers of the invention does not bind to its protein target at a pH higher than 7.0.

Moreover, as illustrated in the Examples, the aptamers identified by the method of the invention can be used as affinity ligands in the purification of the protein target, because the complex formed by said aptamers and their protein target can be dissociated in mild conditions of elution. Noteworthy, said aptamers may be used for the purification of the protein target from very complex media such as body fluids, including blood, plasma, milk and derivatives thereof.

Accordingly, a further object of the invention is an aptamer obtainable or obtained by the methods of the invention.

In a specific aspect, the invention relates to an aptamer which specifically binds to a protein target comprising a histidine-containing surface domain. Said protein target may be as defined above. In particular, such protein target may be selected among proteins comprising a histidine-containing domain and having at least one of the following features:

The protein target has an isoelectric point (pI) of less than 7.5, preferably less than 7.0 such as a pI of 4.0 to 6.9.
The protein target is devoid of any surface domain with positive electrostatic potential at pH of more than 7.0.

In some embodiments, the protein target is selected from the group consisting of fibrinogen, immunoglobulins and fragments or variants thereof as well as any Fc-containing proteins such as Fc-fusion proteins. For instance, the target protein may be selected from the group consisting of plasma human fibrinogen, recombinant human fibrinogen, variants of fibrinogen, fragments of fibrinogen, plasma human IgG, recombinant human IgG, chimeric IgG, humanized IgG, variants of human IgG, Fc fragment from human IgG and Fc variants from human IgG.

The aptamer of the invention may be a deoxyribonucleic acid (DNA) or a ribonucleic acid (RNA). Preferably, the aptamer is a DNA aptamer. The aptamer may comprise one or several chemically-modified nucleotides as detailed herein. In certain embodiments, the aptamer may comprise a modified nucleotide at its 3'-end or/and 5'-end only (i.e. the first nucleotide and/or the last nucleotide of the aptamer is/are the sole chemically-modified nucleotide(s)). Preferably, said modified nucleotide may enable the grafting of the aptamer onto a solid support, or the coupling of said aptamer with any moiety of interest (e.g. useful for detection or immobilization). In some embodiments, the aptamer of the invention is devoid of any 5-modified deoxyuridine or boronic acid-modified nucleotides. In some other embodiments, the aptamer of the invention is devoid of any chemically-modified nucleotides.

As mentioned above, the affinity of the aptamer to its protein target may be pH-dependent.

In a particular embodiment, the invention relates to an aptamer directed against fibrinogen, said aptamer being able to bind fibrinogen at a pH lower than 6.8, preferably at a pH lower than 6.8 and higher than 6.0, for instance 6.2-6.6, such as 6.4, without binding to fibrinogen at a pH higher than 7.0 such as 7.4.

In another embodiment, the invention relates to an aptamer directed against Fc fragment from a human IgG, said aptamer being able to bind said Fc fragment at a pH lower than 6.0, preferably at a pH lower than 6.0 and higher than 5.0, for instance at a pH 5.2-5.7, such as 5.5 without binding to Fc fragment at a pH higher than 7.0, preferably higher than 6.0.

The aptamers of the invention find applications in several fields, in particular in the purification and the detection field. In particular, the aptamers of the invention can be used to prepare affinity ligands.

A further object of the invention is thus an affinity ligand comprising an aptamer of the invention. Typically, the affinity ligand of the invention comprises (i) an aptamer moiety, i.e. an aptamer as defined above linked to at least one (ii) non-aptamer entity useful for immobilization on an appropriate substrate. Preferably, the non-entity aptamer is preferably linked to the 5'- or the 3'-end of the aptamer.

In certain embodiment, the affinity ligand may comprise a mean of immobilization linked to the aptamer moiety directly or by a spacer group. Accordingly, the affinity ligand may comprise, or consist of, a compound of formula (IV):

[IMM]-([SPACER])$_p$-[APTAMER] wherein

[APTAMER] denotes an aptamer as defined above,
[SPACER] is a spacer group,
[IMM] is a moiety for the immobilization of the aptamer onto a support and
p is 0 or 1.
p is 0 means that the spacer is absent and that [IMM] is directly linked to [APTAMER], preferably at the 3' or the 5'-end of aptamer.
p is 1 means that the spacer is present and links to [IMM] and [APTAMER].

The spacer group is typically selected to decrease the steric hindrance of the aptamer moiety and improve its accessibility while preserving the aptamer capability of specifically binding to its protein target. The spacer group may be of any type. The spacer may be a non-specific single-stranded nucleotide, and may comprise from 2 to 20 nucleotides in length. Examples of appropriate nucleic spacers are polyA and polyT. In some other embodiments, the spacer may be a non-nucleic chemical entity. For instance, the spacer may be selected from the group consisting of a peptide, a polypeptide, an oligo- or polysaccharide, a hydrocarbon chain optionally interrupted by one or several heteroatoms and optionally substituted by one or several substituents such as hydroxyl, halogens, or $C_1$-$C_3$ alkyl; polymers including homopolymers, copolymers and block polymers, and combinations thereof. For instance the spacer may be selected from the group consisting of polyethers such as polyethylene glycol (PEG) or polypropylene glycol, polyvinylic alcool, polyacrylate, polymethacrylate, polysilicone, and combination thereof. For instance, the spacer may comprise several hydrocarbon chains, oligomers or polymers linked by any appropriate group, such as a heteroatom, preferably —O— or —S—, —NHC(O)—, —OC(O)—, —NH—, —NH—CO—NH—, —O—CO—NH—, phosphodiester or phosphorothioate. Such spacer chains may comprise from 2 to 200 carbon atoms, such as from 5 to 50 carbon atoms or such as 2 to 20 atom carbons. Preferably, the spacer is selected from non-specific oligonucleotides, hydrocarbon chains, polyethers, in particular polyethylene glycol and combinations thereof.

A further object of the invention is an affinity support comprising a solid support having thereon a plurality of aptamers or affinity ligands as defined above. The solid support may be of any type. For instance, the solid support may be a polymeric gel, filter or membrane. In particular, the solid support may be composed of agarose, cross-linked agarose, cellulose or synthetic polymers such as polyacrylamide, polyethylene, polyamide, polysulfone, and derivatives thereof. Such supports may be suitable for the purification of the protein target. For instance, the solid support may be a support for chromatography, in particular for liquid affinity chromatography.

Accordingly, the aptamer, the affinity ligand and the affinity support may be used in the purification of the protein target.

Alternatively, the aptamers and the affinity ligands of the invention may be used in the diagnostic and detection field. In particular, the aptamers and the affinity ligands of the invention may be useful for the diagnostic or the prognostic of diseases or disorders associated with a variation of the expression of the protein target.

In another aspect, the aptamers of the invention may be also used in the treatments of disorders involving the protein target.

Further aspects and advantages of the present invention are disclosed in the following experimental section, which should be regarded as illustrative and not limiting the scope of the present application.

List of sequences

| SEQ ID NO | Sequences | Description |
|---|---|---|
| 1 | GGGTCAATGCCAGGTCTCGGACCTGGA ATCCGCCACCCGCATTAGAACCAGGGT TGACATCGGCTCGCAAGCAGTC | Anti-fibrinogen aptamer (aptamer A5-1) |
| 2 | GGGTCAATGCCAGGTCTCAACTTTCGC GTGTGGTTGGTAGGGCTAGGTGTATAC GCATATCGGCTCGCAAGCAGTC | Anti-fibrinogen aptamer (aptamer A5-2) |
| 3 | GGGTCAATGCCAGGTCTCGGACCTGGA ATCCGCCACCCGCATTAGAACCAGGGT TGAC | Anti-fibrinogen aptamer-core sequence of SEQ ID NO: 1 (aptamer A5-1.9) |
| 4 | CGCGTGTGGTTGGTAGGGCTAGGTGTA TACGCAT | Anti-fibrinogen aptamer-core sequence of SEQ ID NO: 2 (aptamer A5-2.9) |
| 5 | GGGTCAATGCCAGGTCTCCCCAGCCTC ATCTCACGGCATAGTCTCGCCACACTG GAAATCGGCTCGCAAGCAGTC | Anti-Fc aptamer (aptamer A6-2) |
| 6 | GGGTCAATGCCAGGTCTCCACGGTATA GTCTCGCCCAGTGCCCTTTGTTGGACT TCCTATCGGCTCGCAAGCAGTC | Anti-Fc aptamer (aptamer A6-8) |

Example 1: Identification of Anti-Fibrinogen Aptamers by the Method of the Invention 1. Material and Method
Oligonucleotide Library
The ssDNA library used to perform SELEX process consisted of a 40-base random region flanked by two constant 18-base primer regions.
Fibrinogen
The protein target was human fibrinogen. Different sources of human fibrinogen were used during Selex process:
Human fibrinogen: Two preparations of human fibrinogen were used as purified composition from human plasma with a purity of 95% and 99.9%, respectively.

Transgenic fibrinogen: Transgenic Fibrinogen was purified from the milk of transgenic cows to 97% purity.
SELEX Protocol
Fibrinogen (97% pure transgenic Fibrinogen for round 1 to 3 and 95% pure plasmatic Fibrinogen for round 4&5 and 99.9% pure plasmatic Fibrinogen for round 6 to 8) was immobilised on an affinity resin, while the amount of target immobilised on the resin continuously decreased from round 1 to 8 (see FIG. 2).

The immobilised target was incubated with the ssDNA library/pool at decreasing concentrations using as selection buffer (50 mM MOPS pH 6.30, 150 mM NaCl, 5 mM $MgCl_2$) at decreasing incubation time (see table of FIG. 2).

The fibrinogen/ssDNA containing resin was recovered and washed with selection buffer during round 1 & 2 and wash buffer containing 50 mM MOPS pH 6.30, 500 mM NaCl, 5 mM $MgCl_2$ from round 3 to 8 (see table of FIG. 2). After washing, the bound ssDNA was eluted using elution buffer (50 mM Tris-HCl pH 7.40, 200 mM EDTA). Before every round (except the first round) a counter selection step was performed by incubating the ssDNA pool with the affinity resin in order to prevent the enrichment of anti-support aptamers. The parameters of the SELEX protocols are depicted in FIG. 2.

Determination of the Binding Affinity of Aptamers by SPR
The selected aptamer was synthetized with Biotin and a triethylene glycol spacer at the 5' end of the oligonucleotide. A 1 µM solution of the aptamer was prepared using the SELEX selection buffer. The aptamer solution was heated to 90° C. for 5 min, incubated on ice for 5 min and equilibrated to room temperature for 10 min. The preparation was injected on a streptavidin coated sensor chip SA of Biacore T200 instrument (GE Healthcare) at a flow rate of 10 µl/min for 7 min. Then, different concentrations of the target were injected to the immobilised aptamer at 30 µl/min for 1 minute. After dissociation for 1-2 min a wash step was performed by injecting a suitable wash buffer at 30 µl/min for 1 min. For elution, a suitable elution buffer was injected at 30 µl/min for 1-2 min. Finally the sensor chip was regenerated by injection of 50 mM NaOH at 30 µl/min for 30 sec. During the course of the experiment the response signal was recorded in a sensorgram.

2. Results
The SELEX method of the invention enables to identify 67 anti-fibrinogen aptamer candidates, among which aptamers of SEQ ID NO:1 and SEQ ID NO:2 displayed a high affinity for both plasma and transgenic human fibrinogen. These aptamers were shown to bind human fibrinogen in a pH dependent manner. The core sequences of these aptamers (namely the minimal sequence binding to fibrinogen) were determined. The aptamer of SEQ ID NO:3 corresponds to the core sequence of aptamer of SEQ ID NO:1. The aptamer of SEQ ID NO:4 is the core sequence of aptamer of SEQ ID NO:2. FIGS. 3A-3D show the binding profile obtained for the core sequences of aptamers of SEQ ID NO:1 and NO:2 by SPR. Aptamers of SEQ ID NO:3 and 4 are able to specifically bind to transgenic fibrinogen and plasma fibrinogen at pH 6.3 in a dose-dependent manner, as evidenced by the increase of the signals when the concentration of fibrinogen was increased. The complex between the aptamers and fibrinogen were not significantly dissociated by the increase of NaCl concentration. On the other hands, the injection of a buffer at pH 7.4 enabled to dissociate the complex between the aptamers and whereby fibrinogen was eluted.

Indeed, the aptamers obtained by the method of the invention bind to fibrinogen in a pH-dependent manner. Such a result is illustrated in FIGS. 4A and 4B for aptamers of SEQ ID NO:3 and SEQ ID NO:4 respectively. The binding level of fibrinogen decreased when pH increased. The highest binding was observed at pH 6.3. The aptamers did not bind to fibrinogen for pH higher than 6.8.

Example 2: Comparative Example

The same SELEX process as in Example 1 was carried out except that the oligonucleotide library was contacted with the purified composition of plasmatic fibrinogen (95%) for round 1 to 4 and with transgenic Fibrinogen from round 5 to 9 using a selection buffer at pH 7.40 and the elution was performed with an aqueous solution comprising 200 mM EDTA at pH 7.40. The process led to the identification of several aptamers. The binding properties of said aptamers were tested by SPR. Each aptamer of interest was immobilized on the chip of the SPR and then contacted with the purified composition of fibrinogen. In order to identify the protein from the purified composition which has been bound by the aptamer, several antibodies were tested. Notably, anti-fibrinogen antibodies did not induce any increase of the signal, showing that the protein captured by the aptamer was not human fibrinogen. Indeed, the aptamers selected by the process did not bind to human fibrinogen, but to a contaminant accounting for less than 1% in the starting purified plasma fibrinogen and not present in the transgenic fibrinogen preparation.

Example 3: Preparation of Affinity Supports from Aptamers Identified by the Method of the Invention 1. Material and Method
Affinity Supports Two affinity supports were prepared by grafting aptamers on NHS-activated Sepharose (GE Healthcare). The first affinity support (affinity support n° 1) was prepared by grafting aptamers of SEQ ID NO:3 (aptamer A5-1.9) comprising a C6 spacer with a terminal amino group at its 5' end and an inverted deoxy-thymidine at its 3' end. The second affinity support (affinity support n° 2) was prepared by grafting aptamers of SEQ ID NO:4 (aptamer A5-2.9) comprising comprising a C6 spacer with a terminal amino group at its 5' end and an inverted deoxy-thymidine at its 3' end.

1 volume of NHS activated Sepharose gel placed in a column was rinsed with at least 10 volumes of a cold 0.1 M HCl solution, then equilibrated with at least 8 volumes of cold 100 mM acetate pH 4.0 solution.

After a 3 min-2000 g centrifugation, the supernatant is removed and drained gel is re-suspended with 2 volumes of aptamer in 100 mM acetate pH 4.0 solution. This suspension is incubated for 2 hours at room temperature under stirring.

Then, 1 volume of 200 mM Borate pH 9 is added, this suspension is incubated at room temperature under stirring for 2 h30.

After a 3 min-2000 g centrifugation, the supernatant is discarded. Drained gel is re-suspended in 2 volumes of Tris-HCl 0.1M pH 8.5 solution. Suspension is incubated at +4° C. under stirring overnight.

After incubation, and a 3 min-2000 g centrifugation, the supernatant is discarded. The gel is alternatively washed with 2 volumes of Sodium acetate 0.1M+NaCl 0.5M pH 4.2 and 2 volumes of a Tris-HCl 0.1M pH 8.5 solution. This washing cycle is repeated once.

After a 3 min-2000 g centrifugation supernatant is removed. The drained gel is re-suspended in 2 volumes of equilibration buffer.

Example 4: Purification of Fibrinogen from Semi Purified Fibrinogen Solution on the Affinity Support of Examples 3

1. Material and Method
Conditions of the Affinity Chromatography

Affinity support n° 1: Thawed semi purified fibrinogen solution (IP1: Fibrinogen Intermediate Product 1) obtained from human plasma was diluted 10 times in the binding buffer and was pH adjusted to 6.3. Diluted IP1 was subjected to a chromatography steps on support n° 1. This step was repeated once to obtain enough fibrinogen quantity for ultrafiltration step.

Affinity support n° 2: Thawed semi purified fibrinogen solution (IP1: Fibrinogen intermediate product 1) obtained from human plasma was diluted 10 times in the binding buffer and pH was adjusted to 6.3. Diluted IP1 was subjected to a chromatography steps on support n° 2. This step was repeated once to obtain enough fibrinogen quantity for ultrafiltration step.

The conditions of the affinity chromatography are summarized for each affinity support:

| | Affinity support n°1 grafted with aptamer moieties of SEQ ID NO: 3 (A5-1.9) | Affinity support n°2 grafted with aptamer moieties of SEQ ID NO: 4 (A5-2.9) |
|---|---|---|
| Binding buffer | MOPS 50 mM, $MgCl_2$ 5 mM, NaCl 150 mM, pH 6.3 | MOPS 50 mM, NaCl 150 mM, pH 6.3 |
| Washing buffer | None | MOPS 50 mM, NaCl 2M, pH 7.4 |
| Elution buffer | MOPS 50 mM, NaCl 150 mM, pH 7.4 | MOPS 50 mM, $MgCl_2$ 2M, pH 7.4 |

For each affinity support, fibrinogen was eluted in mild conditions by modification of the buffer composition.

For both chromatography on Affinity support n° 1 and n° 2:2 eluate fractions were generated and pooled for ultrafiltration step.

Conditions of the Ultrafiltration

For each affinity support, pool of eluate fractions were subjected to an ultrafiltration 100 kDa in order to concentrate Fibrinogen and to formulate in sodium citrate 10 mM, arginine 20 g/L at pH 7.4.

Analytical Methods

| Proteins | Titration methods |
|---|---|
| Fibronectin, antigenic Fibrinogen | Nephelometry |
| Factor II, Factor XI, Factor XIII, Plasminogen | Elisa |
| Fibrinogen clotting activity | Coagulation assay (von Clauss method) |

2. Results

The results are shown in FIGS. 7A-7B and 7C-7D. FIGS. 7A and 7B show the chromatography profile obtained for the fibrinogen purification from semi purified fibrinogen solution on the affinity support n° 1 and n° 2 respectively. Fibrinogen was eluted by increasing the pH to 7.4 and by adding $MgCl_2$ for affinity support n° 2 and by suppressing $Mg^{2+}$ for affinity support n° 1. The electrophoresis analysis of the fractions obtained by chromatography (FIGS. 7C and 7D) showed that contaminants present in the loaded material (IP1) are drastically removed with almost only Fibrinogen visible in the eluate. Additionally, electrophoresis analysis in reducing conditions shows that Fibrinogen in the eluate is in a native form with no visible degradation (Aα1 is the most important band of Aα bands)

Yields and fibrinogen concentration obtained are summarized in the table below:

| | Affinity support n°1 | Affinity support n°2 |
|---|---|---|
| Chromatography yield (%) | 51 | 71 |
| Concentration of antigenic fibrinogen | 13.1 | 14.2 |

| | Affinity support n°1 | Affinity support n°2 |
|---|---|---|
| obtained after ultrafiltration (mg/ml) | 5 | |

Active Fibrinogen is demonstrated by a ratio between coagulant Fibrinogen and antigenic Fibrinogen close to 1. Analysis on the starting material and the resulting purified fibrinogen prepared with both affinity supports are detailed in the following table:

| | clotting activity Fibrinogen g/L | Fibrinogen/ratio clotting/antigenic |
|---|---|---|
| Starting material (IP1 fibrinogen) | 17.6 | 1.17 |
| Purified Fibrinogen concentrate-Support n°1 | 13.9 | 1.06 |
| Purified Fibrinogen concentrate-Support n°2 | 14.5 | 1.02 |

For both purified Fibrinogen, the ratio between clotting and antigenic fibrinogen was about 1.0 for both aptamers. The soft chromatography conditions allowed the preparation of a purified fibrinogen with preserved activity.

The table hereunder shows the contaminant proteins titration in the starting material and the purified fibrinogen fractions:

| Contaminant proteins | semi purified Fibrinogen (starting composition) Concentration | Fibrinogen purified with affinity support n°1 Concentration | Removal | Fibrinogen purified with affinity support n°2 Concentration | Removal |
|---|---|---|---|---|---|
| Fibronectin | 0.55 g/L | 0.02 g/L | 96.3% | 0.02 g/L | 95.1% |
| Factor II | 0.13 mUI/mL | 0.03 mUI/mL | 70.8% | 0.04 mUI/mL | 66.3% |
| Factor XI | 21.0 mUI/mL | 2.8 mUI/mL | 83.8% | 3.6 mUI/mL | 80.8% |
| Factor XIII | 10000 mUI/mL | 10 mUI/mL | 99.9% | 42 mUI/mL | 99.5% |
| Plasminogen | 56 µg/mL | 0.21 µg/mL | 99.5% | 0.21 µg/mL | 99.6% |

A good elimination of contaminants proteins is obtained with a removal from 65% to over than 99% as compared to the starting material.

Chromatography conditions allowed the removal of more than 99.5% of initial plasminogen, which is one of the most problematic contaminant with regards to Fibrinogen stability.

The aptamers identified by the SELEX of the invention are suitable for use as affinity ligand in the purification of fibrinogen by chromatography. Noteworthy, the aptamers identified by the process of the invention enables the selective binding and then the elution of fibrinogen in mild and non-denaturing conditions, while removing most of the possible contaminants.

Example 5: Purification of Fibrinogen by Chromatography from Plasma

Purification on affinity support n° 1: The Plasma was thawed, filtrated 0.45 µm, diluted 10 times in the binding buffer and then pH adjusted to 6.3. Diluted solution was subjected to a chromatography steps on support n° 1.

Purification on affinity support n° 2: The Plasma was thawed, filtrated 0.45 µm, diluted 10 times in the binding buffer and then pH adjusted to 6.3. Diluted solution was subjected to a chromatography steps on support n° 2.

The conditions of the affinity are summarized, for each affinity support, in the table below:

| | Affinity support n°1 grafted with aptamer moieties of SEQ ID NO: 66 (A5-1.9) | Affinity support n°2 grafted with aptamer moieties of SEQ ID NO: 67 (A5-2.9) |
|---|---|---|
| Binding buffer | MOPS 50 mM, MgCl$_2$ 5 mM, NaCl 150 mM, pH 6.3 | MOPS 50 mM, NaCl 150 mM, pH 6.3 |
| Washing buffer | return to baseline with the binding buffer | MOPS 50 mM, NaCl 2M, pH 7.4 |
| Elution buffer | MOPS 50 mM, NaCl 150 mM, pH 7.4 | MOPS 50 mM, MgCl$_2$ 2M, pH 7.4 |
| Regeneration buffer | MOPS 50 mM, MgCl$_2$ 2M, pH 7.4 | same as the elution buffer |

For each affinity support, fibrinogen was eluted in mild conditions by modification of the buffer composition.

2. Results

The results are shown in FIGS. 5A-5B and 6A-6B. FIGS. 5A and 6A show the chromatography profile obtained for the purification of fibrinogen from plasma on the affinity support n° 1 and n° 2 respectively. Noteworthy, most of the contaminant proteins were not retained on the stationary phase whereas fibrinogen bound to the support. Fibrinogen was eluted by increasing the pH to 7.4 and by adding 2 M MgCl$_2$ for affinity support n° 2 and by suppressing Mg$^{2+}$ for affinity support n° 1. The electrophoresis analysis of the fractions obtained by chromatography (FIG. 5B and FIG. 6B) showed that fibrinogen was mostly present in the elution fraction whereas contaminant proteins were present in the non-retained fraction, in the washing fraction or the regeneration fraction. Indeed, the elution fractions migrated as single band. The relative purity (determined by SDS PAGE) of the eluate fibrinogen fractions was greater than 95%. Such results demonstrate that the aptamers of the invention are particularly suitable for a use as affinity ligands in the purification of fibrinogen from complex starting compositions.

Example 6: Identification of Anti-IgG Aptamers by the Method of the Invention

1. Material and Method
Oligonucleotide Library

The ssDNA library used in the SELEX process of the invention consisted of a 40-base random region flanked by two constant 18-base primer regions.
Human Polyclonal IgG-Fc Fragments The protein target used for the SELEX was highly pure human polyclonal IgG, Fc fragment. It was obtained from Jackson ImmunoResearch Laboratories, INC (ref. 009-000-008).
SELEX Protocol During the course of the SELEX, continuously decreasing amounts of highly pure Human IgG, Fc fragment was incubated with the ssDNA library/pool at decreasing concentrations using as selection buffer 50 mM MES pH 5.50, 150 mM NaCl, 5 mM MgCl2 at decreasing incubation times (see table of FIG. 8).

The unbound ssDNA was partitioned from IgG-Fc/ssDNA complexes using nitrocellulose filters. The complex containing filters were washed with selection buffer during round 1, 2, & 3 and wash buffer containing 50 mM MOPS pH 5.50, 500 mM NaCl, 5 mM MgCl2 during round 4 to 6 and wash buffer containing 50 mM MOPS pH 5.50, 1M NaCl, 5 mM MgCl2 during round 7 & 8 (see table of FIG. 8). After washing, the bound ssDNA was eluted using elution buffer (50 mM Tris-HCl pH 7.40, 200 mM EDTA).

Before every round (except the first round) a counter selection step was performed by incubating the ssDNA pool with one nitrocellulose filter in order to prevent the enrichment of anti-nitrocellulose aptamers.

The parameters of the SELEX protocols are depicted in FIG. 8.
Determination of the Binding Affinity of the Identified Aptamers by SPR:

The selected aptamer was synthetized with Biotin and a triethylene glycol spacer at the 5' end of the oligonucleotide. A 1 μM solution of the aptamer was prepared using the SELEX selection buffer. The aptamer solution was heated to 90° C. for 5 min, incubated on ice for 5 min and equilibrated to room temperature for 10 min. The preparation was injected on a streptavidin coated sensor chip SA of Biacore T200 instrument (GE Healthcare) at a flow rate of 10 μl/min for 7 min. Then, different concentrations of the target (Human polyclonal IgG, purified from human plasma with a purity of >95%) were injected to the immobilised aptamer at 30 μl/min for 1 minute. After dissociation for 1-2 min a wash step was performed by injecting a suitable wash buffer at 30 μl/min for 1 min. For elution, a suitable elution buffer was injected at 30 μl/min for 1-2 min. Finally the sensor chip was regenerated by injection of 50 mM NaOH at 30 μl/min for 30 sec. During the course of the experiment the response signal was recorded in a sensorgram.

2. Results

The SELEX method of the invention enables to identify several anti-IgG aptamer candidates, among which aptamers of SEQ ID NO:5 and SEQ ID NO:6. The binding ability of aptamers of SEQ ID NO:5 and 6 to IgG was assessed by SPR.

FIG. 9A shows the binding curves of human polyclonal IgG for aptamers of SEQ ID NO:5 (A6-2) and SEQ ID NO:6 (A6-8) immobilized on a sensor chip. The aptamers were shown to bind to polyclonal IgG at pH 5.5. The injection of a buffer solution at pH 5.50 comprising 2M NaCl did not significantly induce the elution of human polyclonal IgG. The complex between the aptamers and polyclonal IgG was dissociated by increasing the pH of the buffer. Human polyclonal IgG was then released from the complex by an elution buffer at pH 7.40. Similarly to anti-fibrinogen aptamers identified by the method of the invention, the anti-IgG aptamers of the invention specifically bound to their target protein in a pH-dependent manner. The highest binding was obtained for pH 5.30. The binding level decreased, with the increase of pH. No significant binding was observed for pH higher than pH 6.0 (FIG. 9B).

Example 7: Affinity Support and Purification of IgG from Plasma

1. Material and Method
Affinity Support

An affinity support was prepared by grafting aptamers of SEQ ID NO:5 (A6-2) comprising a C6 spacer with a terminal amino group at its 5' end and an inverted deoxythymidine at its 3' end, on NHS-activated Sepharose (GE Healthcare):

1 volume of NHS Sepharose activated gel placed in a column was rinsed with at least 10 volumes of a cold 0,1M HCl solution, then equilibrated with at least 8 volumes of cold 100 mM acetate pH 4.0 solution.

After a 3 min-2000 g centrifugation, the supernatant is removed and drained gel is re-suspended with 2 volumes of an aptamer in 100 mM acetate pH 7.0 solution. This suspension is incubated at room temperature under stirring.

After 2 hours, 1 volume of 200 mM Borate pH 9 is added. This suspension is incubated at room temperature under stirring for 2H30.

After a 3 min-2000 g centrifugation, the supernatant is removed. Drained gel is re-suspended in 2 volumes of 0,1M Tris-HCl pH 8.5 solution. Suspension is incubated at +4° C. under stirring overnight.

After incubation, and a 3 min-2000 g centrifugation, the supernatant is removed. The gel alternatively washed with 2 volumes of 0,1M Sodium acetate+0,5M NaCl pH4.2 and 2 volumes of a 0,1M Tris-HCl pH 8.5 solution. This cycle is repeated once.

After a 3 min-2000 g centrifugation supernatant is removed. Drained gel is re-suspended in 2 volumes of binding buffer.

4 mg of aptamer A6-2 was used to be grafted on 1 ml of resine.
Purification of Polyclonal IgG from Purified Plasma IgG or from Plasma 1.1 ml of affinity support was packed in a Tricorn 5/50 column (GE Heathcare). Purified plasma IgG or plasma were diluted with binding buffer to reach a 0.8-1 g/L IgG in final concentration.

The pH was then adjusted to 5.5 with 1M citric acid and then filtered 0.45 μm before loading onto the column. Chromatography buffers are described in the following table.

|  | Affinity support grafted with aptamers of SEQ ID NO: 5 (Aptamer A6-2) |
| --- | --- |
| Binding buffer | Buffering agent: MES 50 mM NaCl 150 mM, MgCl$_2$ 5 mM, pH 5.5 |
| Elution buffer | Buffering agent: MES 50 mM NaCl 150 mM, MgCl$_2$ 5 mM, pH 7.4 |

The linear flow rate used for the chromatography was 100 cm/h, and the quantity of IgG loaded was targeted to be close to the resin capacity (6.5 g/L of resin).

2. Results

The results are shown in FIGS. 10A-10B. FIG. 10A shows the chromatography profile obtained for the IgG from plasma and pre-purified plasma IgG on an affinity support grafted with aptamer of SEQ ID NO:5. Noteworthy, most of the contaminant proteins were not retained on the stationary phase whereas IgG bound to the support. IgGs were eluted by increasing the pH to 7.4. FIG. 10B shows the analysis by SDS Page of the fractions obtained by chromatography for plasma as starting solution. IgGs were mostly present in the elution fraction (lane 3) whereas contaminant proteins were present in the non-retained fraction (lane 2). The relative purity of the IgG eluted from the affinity column was more than 95% by SDS-PAGE. The high purity of the elution fraction demonstrated the high specificity of the aptamer for IgG. The yield of the chromatography was 82% from pre-purified IgGs and 66% from plasma. Yield could be increased with loading a quantity of IgG below the capacity of the resin.

| Purification with A6-2 aptamer | Quantity of IgG in the loaded material | Quantity of IgG in the eluate | Yield |
| --- | --- | --- | --- |
| Purified IgG | 6.3 mg | 5.2 mg | 82% |
| Plasma | 7.9 mg | 5.2 mg | 66% |

The aptamers identified by the method of the invention thus have binding properties suitable for use in protein purification.

The invention claimed is:

1. An anti-fibrinogen aptamer that is SEQ ID NO:1, SEQ ID NO:2, SEQ ID NO:3 or SEQ ID NO: 4.

2. An affinity ligand comprising the aptamer according to claim 1 immobilized onto a support.

3. An affinity support comprising a solid support comprising thereon at least one affinity ligand as defined in claim 2.

4. The affinity support of claim 3, wherein the solid support is a polymeric gel, filter or membrane.

5. The affinity support of claim 3, wherein the solid support comprises a polymer selected from the group consisting of agarose, cross-linked agarose, cellulose, polyacrylamide, polyethylene, polyamide, and polysulfone.

6. The affinity ligand of claim 2, wherein the aptamer is SEQ ID NO: 3.

7. The affinity support of claim 3, wherein the aptamer is SEQ ID NO: 3.

8. The affinity ligand of claim 2, wherein the aptamer is SEQ ID NO: 3 comprising a C6 spacer with a terminal amino group at the 5' end and an inverted deoxy-thymidine at the 3' end.

9. The affinity ligand of claim 4, wherein the affinity ligand is grafted onto NHS-activated Sepharose to form an affinity support.

* * * * *

```
SEQUENCE LISTING

<160> NUMBER OF SEQ ID NOS: 6

<210> SEQ ID NO 1
<211> LENGTH: 76
<212> TYPE: DNA
<213> ORGANISM: Artificial
<220> FEATURE:
<223> OTHER INFORMATION: Aptamer

<400> SEQUENCE: 1
gggtcaatgc caggtctcgg acctggaatc cgccacccgc attagaacca gggttgacat        60
cggctcgcaa gcagtc                                                       76

<210> SEQ ID NO 2
<211> LENGTH: 76
<212> TYPE: DNA
<213> ORGANISM: Artificial
<220> FEATURE:
<223> OTHER INFORMATION: Aptamer

<400> SEQUENCE: 2
gggtcaatgc caggtctcaa ctttcgcgtg tggttggtag ggctaggtgt atacgcatat        60
cggctcgcaa gcagtc                                                       76

<210> SEQ ID NO 3
<211> LENGTH: 58
<212> TYPE: DNA
<213> ORGANISM: Artificial
<220> FEATURE:
<223> OTHER INFORMATION: Aptamer

<400> SEQUENCE: 3
gggtcaatgc caggtctcgg acctggaatc cgccacccgc attagaacca gggttgac          58

<210> SEQ ID NO 4
<211> LENGTH: 34
<212> TYPE: DNA
<213> ORGANISM: Artificial
<220> FEATURE:
<223> OTHER INFORMATION: Aptamer
```

```
<400> SEQUENCE: 4
cgcgtgtggt tggtagggct aggtgtatac gcat                                34

<210> SEQ ID NO 5
<211> LENGTH: 75
<212> TYPE: DNA
<213> ORGANISM: Artificial
<220> FEATURE:
<223> OTHER INFORMATION: Aptamer

<400> SEQUENCE: 5
gggtcaatgc caggtctccc cagcctcatc tcacggcata gtctcgccac actggaaatc    60
ggctcgcaag cagtc                                                     75

<210> SEQ ID NO 6
<211> LENGTH: 76
<212> TYPE: DNA
<213> ORGANISM: Artificial
<220> FEATURE:
<223> OTHER INFORMATION: Aptamer

<400> SEQUENCE: 6
gggtcaatgc caggtctcca cggtatagtc tcgcccagtg ccctttgttg gacttcctat    60
cggctcgcaa gcagtc                                                    76
```